US009488588B2

(12) United States Patent
Palmieri et al.

(10) Patent No.: US 9,488,588 B2
(45) Date of Patent: Nov. 8, 2016

(54) GEMSTONE REGISTRATION SYSTEM

(71) Applicant: Gemological Appraisal Association, Inc., New York, NY (US)

(72) Inventors: Angelo W. Palmieri, New York, NY (US); Donald A. Palmieri, New York, NY (US)

(73) Assignee: GEMLOGICAL APPRAISAL ASSOCIATION, INC., New York, NY (US)

( * ) Notice: Subject to any disclaimer, the term of this patent is extended or adjusted under 35 U.S.C. 154(b) by 0 days.

(21) Appl. No.: 14/810,935

(22) Filed: Jul. 28, 2015

(65) Prior Publication Data

US 2016/0025643 A1 Jan. 28, 2016

Related U.S. Application Data

(63) Continuation of application No. 13/542,100, filed on Jul. 5, 2012, now Pat. No. 9,128,062.

(60) Provisional application No. 61/504,599, filed on Jul. 5, 2011, provisional application No. 61/585,528, filed on Jan. 11, 2012.

(51) Int. Cl.
*G01N 21/00* (2006.01)
*G01N 21/87* (2006.01)

(52) U.S. Cl.
CPC ........... *G01N 21/87* (2013.01); *G01N 2201/02* (2013.01); *G01N 2201/0633* (2013.01); *G01N 2201/06113* (2013.01)

(58) Field of Classification Search
CPC ........ G01N 21/87; G01N 21/00; B24B 9/16; H04N 7/18
See application file for complete search history.

(56) References Cited

U.S. PATENT DOCUMENTS 3,947,120 A 3/1976 Bar-Issac et al.
3,975,097 A 8/1976 Minto
4,517,770 A * 5/1985 Leibowitz ................. B24B 9/16 451/279
5,124,935 A 6/1992 Wallner et al.
5,572,314 A 11/1996 Hyman et al.
5,828,405 A * 10/1998 Vanier .................. G01N 33/381 348/161

(Continued)

FOREIGN PATENT DOCUMENTS

CA 2325130 5/2002
EP 0 042 361 6/1981
WO WO 92/09882 11/1991

OTHER PUBLICATIONS

Gemprint, Gemprint Demo video, May 3, 2011. [online] [retrieved on Oct. 6, 2012], Retrieved from the Internet: <http://www.youtube.comiwatch?v=gDWYR55MxBO>, entire video.

*Primary Examiner* — Tarifur Chowdhury
*Assistant Examiner* — Jamil Ahmed
(74) *Attorney, Agent, or Firm* — Leason Ellis LLP

(57) ABSTRACT

A device for producing a reproducible identification pattern of a polished gemstone includes light directing means for directing a focused beam of light onto a gemstone orientated in a particular known manner to produce an output of the internal refraction and reflection characteristics of the gemstone including reflected light beams having particular locations, sizes and intensities. The device also includes automated means for changing a position of the gemstone relative to the focused beam of light; and also a means for recording the output in a manner to record the relative size and location of the reflected light beams.

23 Claims, 20 Drawing Sheets

400 660 1237 1900 510 1910 1625 1725 730 720 1625 1700 1500 1600 680

(56) References Cited

U.S. PATENT DOCUMENTS 6,211,484 B1 4/2001 Kaplan et al.
6,239,867 B1 * 5/2001 Aggarwal .............. G01N 21/87 356/30
6,980,283 B1 12/2005 Aggarwal
7,239,739 B2 7/2007 Lapa et al.
7,915,564 B2 3/2011 Kaplan et al.
8,705,018 B2 4/2014 Benderly et al.
2001/0006415 A1 7/2001 Dinu et al.
2006/0196858 A1 9/2006 Barron et al.
2010/0092067 A1 4/2010 Ellawand

* cited by examiner

GEMSTONE REGISTRATION SYSTEM

CROSS-REFERENCE RELATED APPLICATIONS

The present application is a continuation of U.S. patent application Ser. No. 13/542,100, filed Jul. 5, 2012, which claims priority to and the benefit of U.S. Patent Application No. 61/585,528, filed Jan. 11, 2012 and U.S. Patent Application Ser. No. 61/504,599, filed Jul. 5, 2011 which are hereby incorporated by reference in their entirety. The present invention also relates to gemstone registration systems disclosed in U.S. Pat. No. 5,124,935; U.S. Pat. No. 5,828,405; and U.S. published patent application No. 2010/0092067, each of which is hereby incorporated by reference in its entirety.

TECHNICAL FIELD

The present invention relates to a system for classifying and recording information with respect to gemstones and providing an owner with an accurate optical identification of the gemstone and provides wholesale and retail establishments, law enforcement, government, and insurance agencies with a verification system.

BACKGROUND

Gemstones have their own unique optical response and this optical response can be used for accurate identification of the gemstones. In this regard, U.S. Pat. No. 3,947,120 discloses an arrangement for providing an optical fingerprint of a gemstone where a laser beam is focused on a gemstone and the optical response of the gemstone is recorded on a recording medium, preferably a photographic medium. This arrangement provides a fingerprint of the gemstone which is reproducible and has been held by the courts to be sufficient evidence to prove that the gemstone under consideration having a certain optical response is the same as a previously identified gemstone having essentially the same optical response.

This prior art structure used a photographic medium and the actual record was sensitive to the exposure period as well as the power of the laser.

European Application No. 0 042 361 discloses a device for producing a reproducible identification pattern of a polished gemstone in which collimated light is directed onto the gemstone and the directions of the refracted and reflected light beams are determined.

Applicant's own PCT application No. PCT/CA91/00424 discloses improvements to systems for recording the optical fingerprint of gemstones.

Applicant's previous systems were largely manual based systems and there is a need for a more automated system that provides a number of new features that both make the gem registration process more reliable and simpler.

SUMMARY

In one embodiment of the present invention, a device for producing a reproducible identification pattern of a polished gemstone includes light directing means for directing a focused beam of light onto a gemstone orientated in a particular known manner to produce an output of the internal refraction and reflection characteristics of the gemstone including reflected light beams having particular locations, sizes and intensities. The device also includes automated means for changing a position of the gemstone relative to the focused beam of light. The device further includes a means for recording the output in a manner to record the relative size and location of the reflected light beams.

In another embodiment, a device according to the present invention for producing a reproducible identification pattern of a polished gemstone includes a housing having a lid and a platform that is covered by the lid when the lid is in a closed position. The device also includes light directing means for directing a focused beam of light onto a gemstone orientated in a particular known manner to produce an output of the internal refraction and reflection characteristics of the gemstone including reflected light beams having particular locations, sizes and intensities. Automated means for changing a position of the gemstone relative to the focused beam of light is provided. The automated means includes a transparent element on which the gemstone is oriented and is configured to move the transparent element and the gemstone along two axes. The device also includes means for recording the output in a manner to record the relative size and location of the reflected light beams, wherein the output is displayed on a substrate that is visible through a window formed in the platform of the housing.

In addition, a centering mechanism is provided and is disposed on the platform and is configured to contact and center the gemstone which in oriented on a platform so as to cause the gemstone to be axially aligned with the beam of light. The centering mechanism moves between a first position and a second position, the first position being one in which the centering mechanism is offset from the beam of light, the second position being on in which a centering tip of the centering mechanism that contacts and centers the gemstone is in registration and aligned with the beam of light.

The present invention also provides a device that is configured for analyzing a gemstone and determining whether the gemstone is in fact a diamond or a diamond simulant based on detected characteristics.

These and other aspects, features and advantages shall be apparent from the accompanying Drawings and description of certain embodiments of the invention.

DETAILED DESCRIPTION OF CERTAIN EMBODIMENTS

Figure 1:
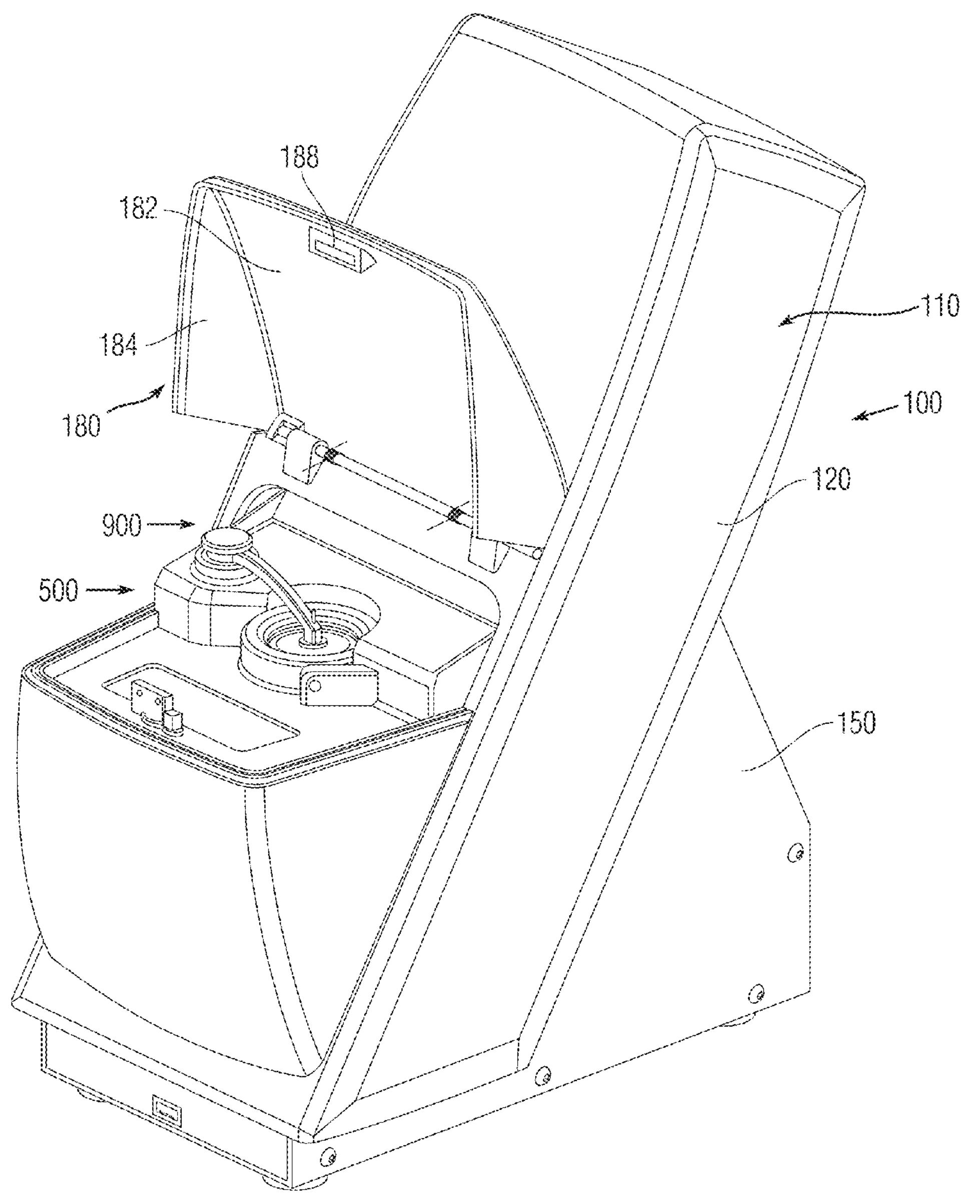
FIG. 1 is front perspective view of gem registration device according to one embodiment of the present invention in an open position.
Figure 2:
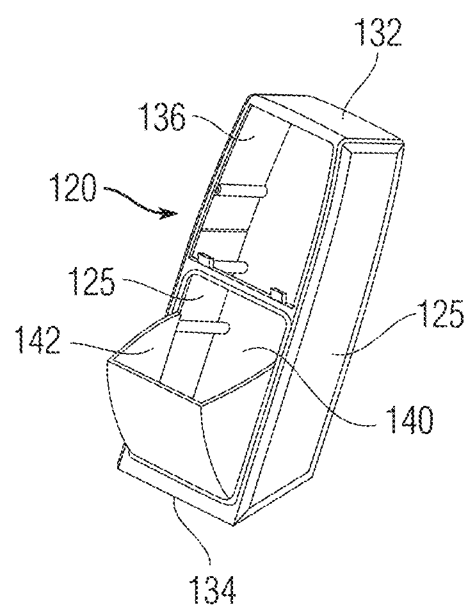
FIG. 2 shows a front cover part of the housing of the device.
Figure 3:
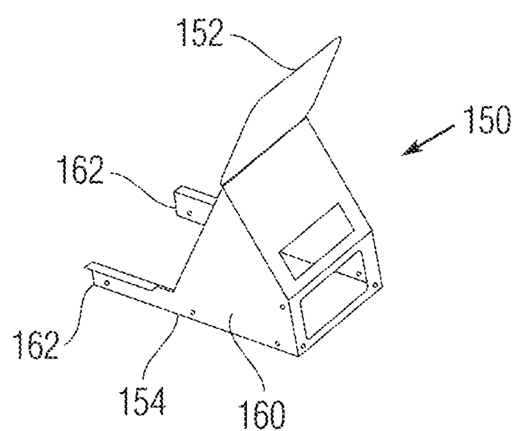
FIG. 3 shows a back cover part of the housing of the device.

FIG. 1 shows a gemstone registration device (system) 100 according to one embodiment of the present invention in a fully assembled condition and in particular, the device 100 is in the form of a device for producing an optical pattern by exposing a gemstone to a beam of light.

As shown in FIGS. 1-12, the device 100 includes a housing 110 that contains the working components of the device 100 and provides a compact, visually pleasing product. The housing 110 is formed of a number of individual parts that are mated together to form the assembled housing 110. More particularly, the housing 110 includes a cover 120 that is formed of a first cover part 130 and a second cover part 150. The first cover part 130 represents a forward portion of the cover 120, while the second cover part 150 represents a rear portion of the cover 120.

The first cover part 130 is a substantially hollow structure that has a top end 132 and an opposing bottom end 134 and includes a front face 136. The top end 132 is a closed end, while the bottom end 134 is an open end. The first cover part 130 is generally in the form of a three sided box-like structure with the bottom end 134 being open as recited above to permit objects to be inserted into the interior of the first cover part 130. Along the front face 136, the first cover part 130 has an opening 140 formed therein. In addition, the first cover part 130 has an extension 142 that protrudes outwardly from the first cover part 130 and is in communication with the opening 140. The extension 142 can be an integral part and is open along a top thereof so as to allow access to the interior of the first cover part 130 through the opening 140. The top edge of the extension 142 can be planar. In the illustrated embodiment, the extension 142 also serves as a base for a lid 180 described below.

As shown in the figures, the first cover part 130 is an upstanding member; however, it is disposed at an angle (other than 90 degrees) relative to the ground surface. In other words, the first cover part 130 does not lie completely perpendicular to the ground but rather is at another angle.

The second cover part 150 mates with the first cover part 130 using conventional means, including fasteners, so as to partially and further enclose the hollow interior space of the first cover part 120. In particular, the second cover part 150 represents the back of the assembled housing, while the first cover part 120 represents the front. The second cover part 150 has a top end 152 and an opposing bottom end 154 and includes spaced apart side walls 160 that define an interior space therebetween. A top section 162 at the first end 152 closes off the back of the first cover part 130 at the top end 132 thereof. The side walls 160 include forward rails 162 that provide a mounting surface for attaching the bottom end 134 of the first cover part 130 to the second cover part 150. Side walls 125 of the first cover part 120 are disposed over the side walls 160 of the second cover part 150.

The lid 180 is pivotally coupled to the first cover part 130 and pivots between an open position in which the lid 180 is disposed generally vertically and the interior space of the extension 142 (lid base) is accessible and a closed position in which the lid 180 seats against the top edge of the extension 142 and can be locked thereto as described herein. As shown, the lid 180 is attached to the front face of the first cover part 120 above the opening 140. The lid 180 has a sloped (arcuate) shaped front wall 182 and a pair of triangular shaped side walls 184. Bottom edges of the front wall 182 and the side walls 184 seat against the top edge (which is generally U-shaped) of the extension 142. Along an inner surface of the front wall 182 a first locking member 188 is disposed. The first locking member 188 locks with another complementary locking member, as described herein, for securing the lid 180 to the housing.

The housing also includes a base or chassis 190 which completes the housing and is disposed along the bottom thereof and represents a ground contacting portion of the housing. The chassis 190 is a substantially planar tray-like structure. The chassis 190 thus includes a bottom wall 192 that represent a floor, a pair of side walls 194, a front wall 196, and a rear wall 198. The rear wall 198 is designed to close off the bottom of the second cover part 140 and the front wall 196 is constructed to attach to a bottom of the front face of the first cover part 120. The floor 192 is a planar surface that seats on a ground surface, such as a table.

When the first and second cover parts 120, 150 and chassis 190 are assembled, the housing only includes one main access point, namely the opening 140. As described herein, the opening 140 receives working components of the device 100 and the lid 180 is opened to access these components as well as to begin the gemstone registration process.

The device 100 also includes a number of sub-assemblies that include the working components of the device 100 that ensure proper positioning of the gemstone and generation of a beam of light for producing a unique optical pattern (the gem's "fingerprint") that is generated when the gemstone is exposed to the beam of light. One sub-assembly concerns the optics and light beam generating means.

Figure 4:
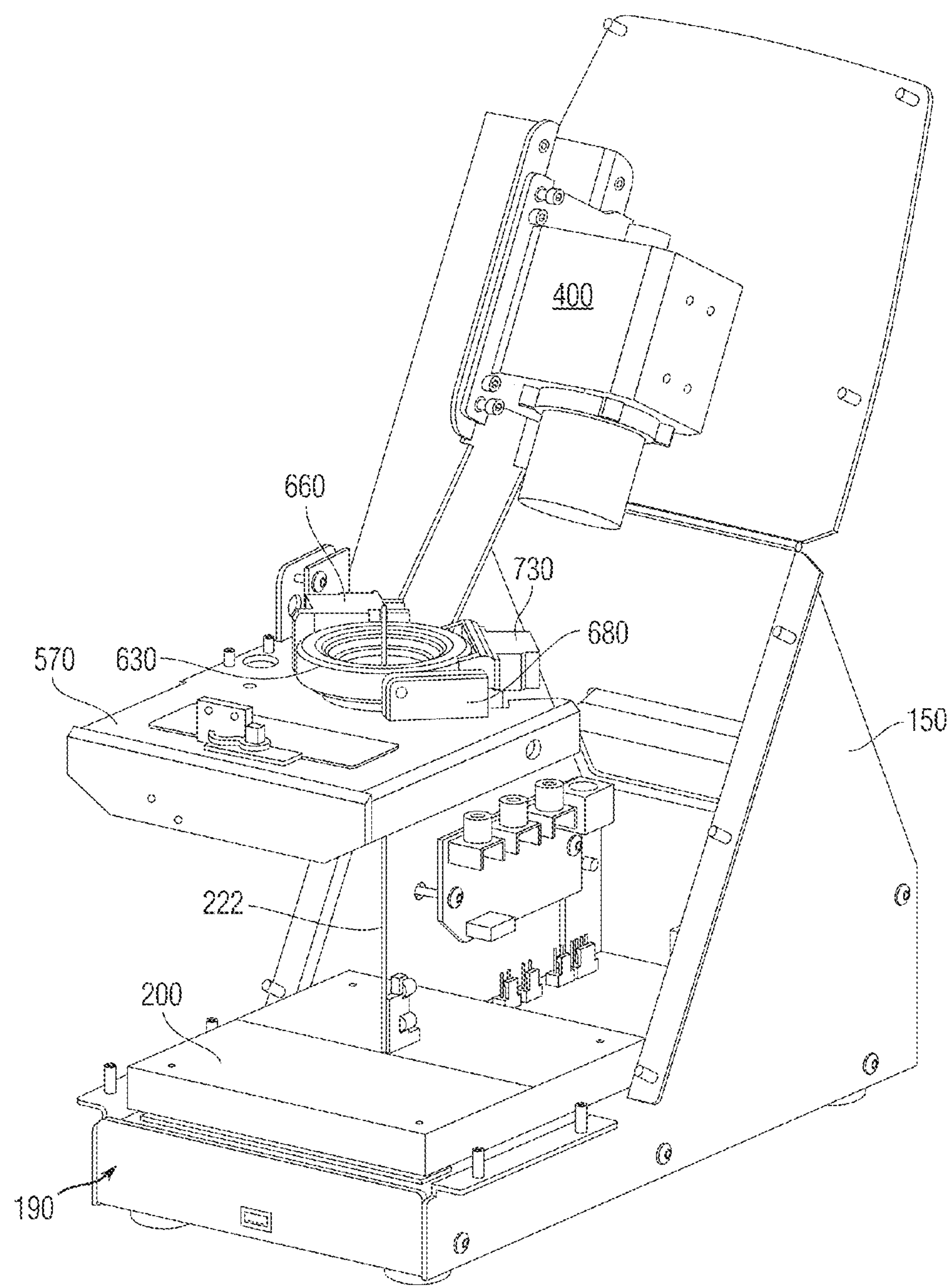
FIG. 4 is a front prospective view with the housing removed to show internal operating parts.
Figure 5:
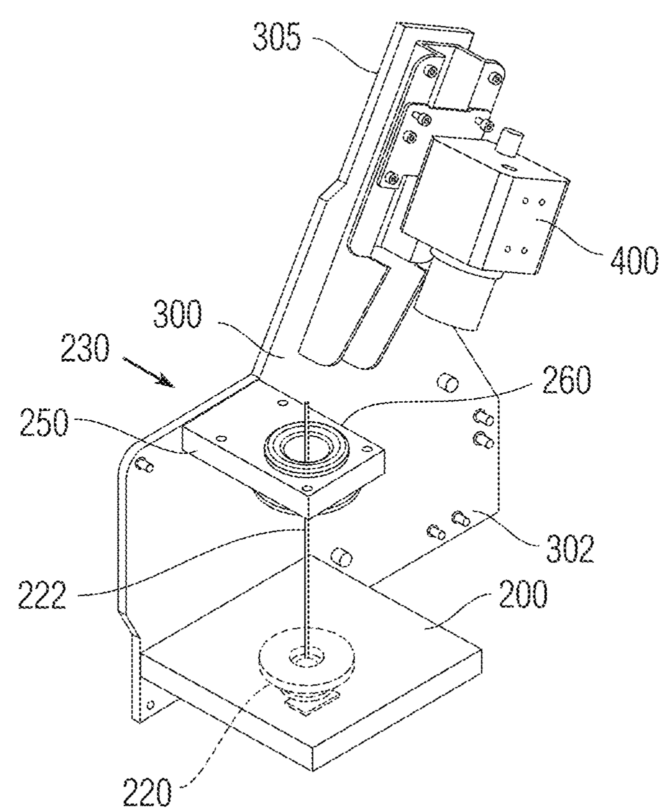
FIG. 5 shows an optical base plate and substrate along with recording means, such as a camera, that are contained with the housing.
Figure 6:
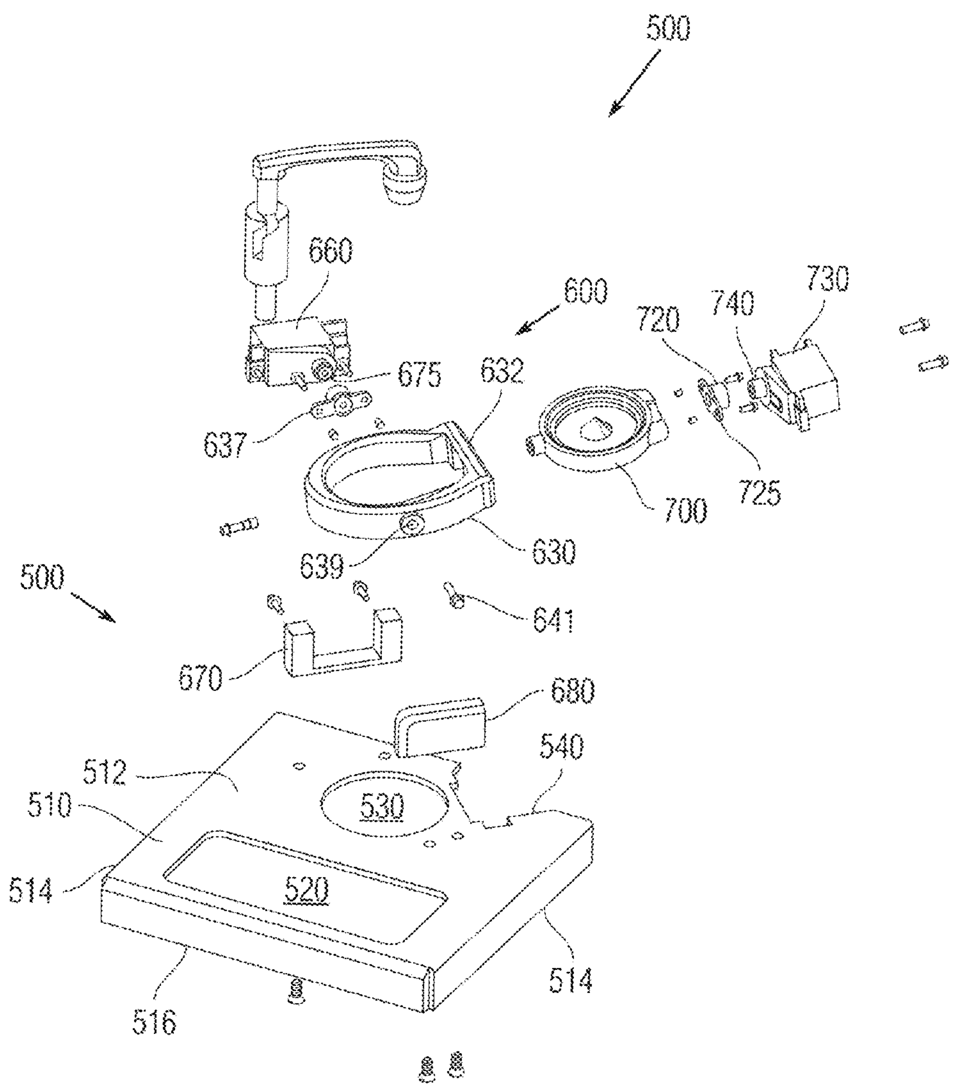
FIG. 6 is an exploded perspective view of a gimbal assembly of the present invention.
Figure 7:
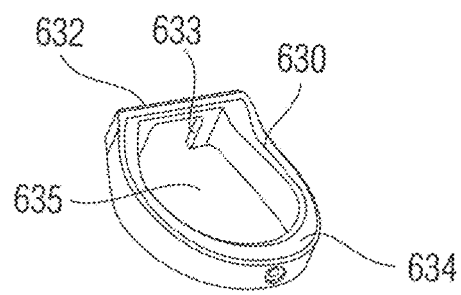
FIG. 7 shows an outer gimbal.
Figure 8:
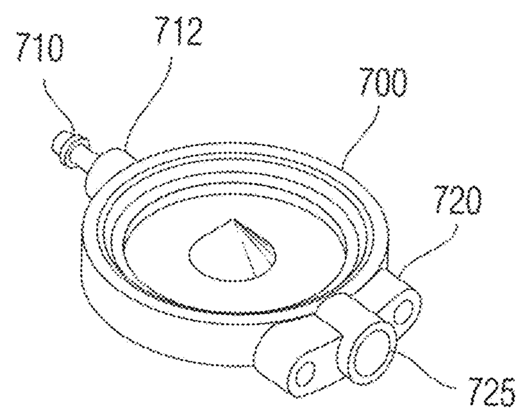
FIG. 8 shows an inner gimbal.
Figure 9:
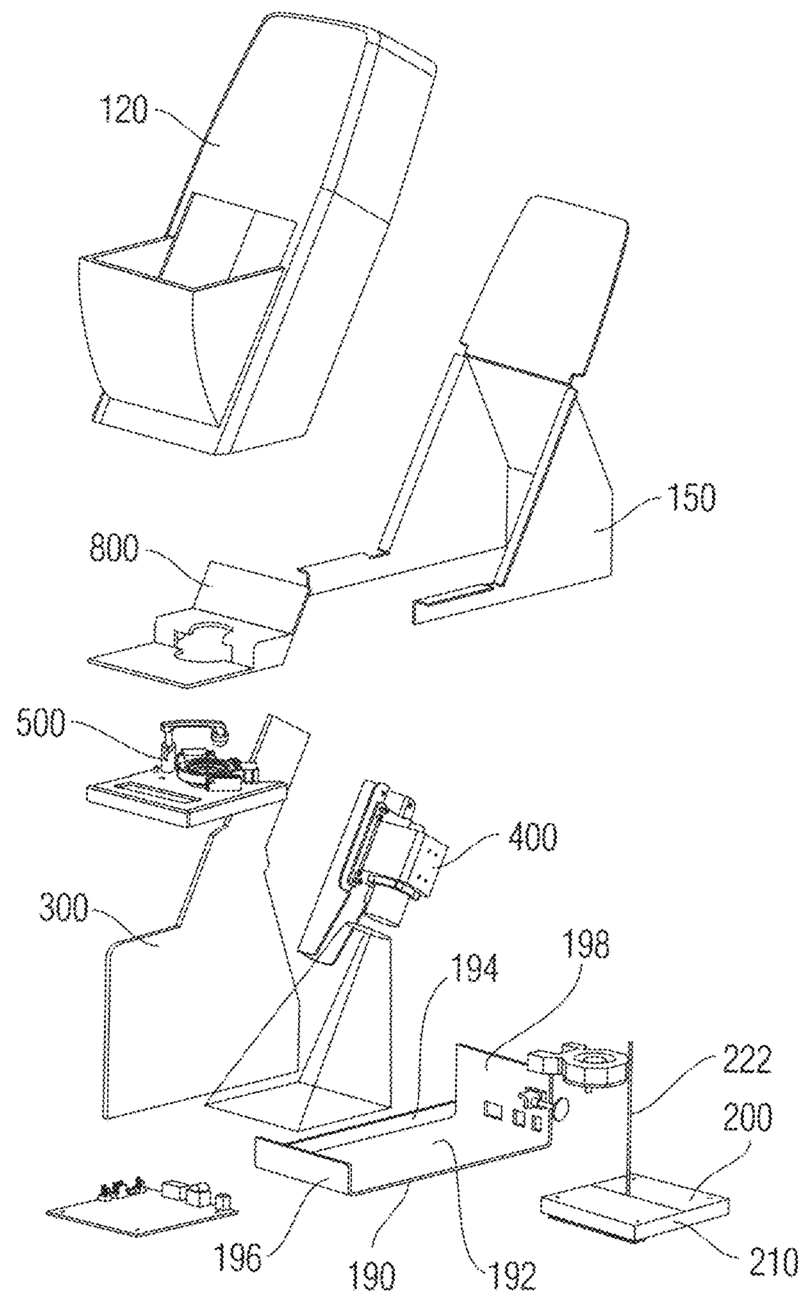
FIG. 9 is an exploded view of the housing and certain inner components of the device.

More specifically as shown in FIGS. 4 and 5, the device 100 includes a planar substrate 200 that is disposed above the floor 192 of the chassis 190. The planar substrate 200 is oriented so that is parallel to the floor 192 but spaced therefrom to permit working components to be disposed thereunderneath between the floor 192 and the substrate 200. The planar substrate 200 has a slit 210 formed therein and generally located in the middle of the substrate 200 and extending from one side to the other side of the generally square shaped substrate 200. This slit 210 allows the focused light beam to exit from its source underneath the substrate 200 and be directed, in a controlled manner, toward the gemstone that rests above the substrate 200 as described herein. In the present embodiment, the light beam is generated centrally relative to the substrate 200 and thus passes through the center of the slit 210. Alternatively, the source of light can be mounted above the substrate 200.

In accordance with the present invention, the light beam generating means is in the form of a laser 220 that is disposed underneath the substrate 200 and aligned with the slit 210 such that the light beam generated by the laser 220 passes through the slit 210 in an unimpeded manner.

The laser 220 is operatively connected to a power source and a controller, such as a printed circuit board (PCB) to allow the controlled operation of the laser 220.

As discussed herein, the device 100 is an electronic device and therefore includes a processor and other electronics to control operation of the various components and to allow processing of data collected by the components of the device 100. Further, the device 100 can be connected to a peripheral device, such as a computer (personal computer) to allow the data collected by the device 100 to be stored (in memory) and processed by the computer which contains a processor that executes code (software) to allow precise control of the gemstone positioning and to allow imaging to be displayed (live video feed) as discussed herein.

Any number of suitable lasers 220 can be used so long as they perform the intended function, including a solid state laser diode. The laser 220 cooperates with an optical arrangement to produce a collimated focused laser light beam 222. The optical arrangement adapts this type of laser to the required, focused, precise light beam suitable to this application. The light beam passes through a narrow opening (slit 210) formed in the substrate 200 which, as described herein, functions as a screen.

As described below, the collimated beam 222 passes though another optical arrangement 230 and subsequently strikes the gemstone that is supported and oriented such that the table of the gemstone is perpendicular to the light beam 222. As shown in FIG. 5, the optical arrangement 230 includes a lens assembly that acts on the light beam 222.

Each gemstone, due to the inherent properties of the gemstone and the cutting of the gemstone, produces a unique optical response which can be distinguished from the optical response from other gemstones. As each gemstone is aligned and centered relative to the beam 222 as described herein, the optical response is inherent to the gemstone such that the optical pattern is consistent. This optical pattern, however, will be at a different rotational position relative to the axis of the light beam as the gemstone position changes and based on the initial placement and orientation of the gemstone.

In order to mount the optical arrangement 230, an optics base plate 300 is provided and is coupled top the second cover part 140 such that it is disposed in an upright position within the housing. The optics base plate 300 is a substantially planar plate that includes a linear bottom edge 302 and a linear front vertical edge 304. The optics base plate 300 also includes an angled arm portion 305 that extends rearwardly and defines the top end of the optics base plate 300. In the illustrated embodiment, the angled arm portion 305 has a generally rectangular shape and is intended to mount equipment as described below.

The substrate 200 is mounted to the optics base plate 300 along one of its edges. The substrate 200 is oriented and mounted perpendicular to the optics base plate 300.

The optics arrangement 230 includes a lens mount base 250 that has an opening. The opening receives a lens 260. In the illustrated embodiment, the lens mount base 250 is a rectangular shaped plate that is attached along one of its ends to the optics base plate 300 above the substrate 200. The lens mount base 250 is disposed substantially perpendicular to the optics base plate 300 and therefore is substantially parallel to the substrate 200. When the lens mount base 250 is mounted to the optics base plate 300, the opening and lens 260 are in registration with the laser beam 222 such that the laser beam 222 passes through lens 260 toward the gemstone that is positioned above the lens 260 as described herein. The lens mount base 250 is disposed along a linear edge of the optics base plate 300 proximate to and forward relative to the angled arm portion 305.

The substrate 200 occupies a significant area of the chassis 190 and in particular, the substrate 200 is located in the forward section of the chassis 190. The remaining portion of the chassis 190 receives other working components of the device 100 such as the electronics, including the printed circuit board, etc. as shown in the figures.

In accordance with the present invention, an imaging/recording device 400 is provided for capturing the optical output response that is unique to the gemstone. According to one embodiment, the device 400 is in the form of a charge couple device, such as a two-dimensional CCD (charge couple device) video camera 400 is positioned and is directed at the screen (substrate) 200. The two-dimensional CCD camera 400 is adjusted to cover the focused optical response provided on the screen 200, allowing this entire image to be captured at the same point in time.

As discussed in Applicant's prior patents, a calibration system can be provided for calibrating the camera position relative to the substrate 200. For example, the screen 200 includes four LEDs located in fixed corner positions of the screen 200. These known precise positions are used to correct for the angular offset of the camera 400 and determine the center of the image. The two-dimensional CCD camera 400 produces a video output signal which is fed to a computer device, such as a personal computer or the like. It will also be appreciated that in other embodiments, a computer module, including a user interface and display can be integrated into the housing of the device 100. This allows the unit to be a true standalone unit.

The camera 400 is mounted to the optics base plate 300 and in particular to the angled arm portion 305 thereof such that the active end of the camera 400 points toward the screen 200. Since the angled part portion 305 is at an angle, the camera 400 is likewise disposed and held at an angle. The camera 400 must be offset from the gemstone location, the optic arrangement and the screen 200 and therefore, the camera 400 is disposed at an angle to allow the optical response formed on the screen 200 to be captured by the camera 400.

The device 100 also includes a gemstone holder assembly 500 that is adjustable to allow the position of the gemstone to be adjusted relative to the light beam 222 in order to allow optimal alignment of the gemstone to be achieved. As discussed herein the assembly 500 is an automated mechanism that allows the gemstone to be adjusted in more than two directions.

The gemstone holder assembly 500 includes a gimbal base 510 that includes a top wall 512, a pair of side walls 514 that extend downwardly from side edges of the top wall 512, and a front wall 516 that extends downwardly from a front edge of the top wall. The front wall 516 can contact and be integral to the side walls 514. The top wall 512 is free of any wall that extends downwardly and is thus a free edge. The gimbal base 510 has a number of openings and cutouts and in particular, the gimbal base 510 includes a first opening 520 that is located along the front of the gimbal base 510. The first opening 520 is an elongated opening and can come in any number of different shapes and sizes so long as the opening 520 permits adequate viewing of the screen 200. The opening 520 is generally rectangular shaped.

Between the first opening 520 and the rear edge of the gimbal base 510, a second opening 530 is formed. The second opening 530 is the opening that is in registration with the lens 260 and therefore, the light beam 222 passes through the second opening 530. For example, the light beam 222 is preferably centrally located within the second opening 530 to allow the light beam to be directed to the gemstone. The second opening 530, in the illustrated embodiment, has a circular shape. The gimbal base 510 includes a cut out 540 that is formed along the rear edge of the gimbal base 510. In the illustrated embodiment, the cut out 540 is located in a corner of the gimbal base 510. The cut out 540 is located proximate the second opening 530.

One side of the gimbal base 510 is coupled to the optics base plate 300 above the lens mount base 250. The lens mount base 250 is disposed under the gimbal base 510 such that the gimbal base 510 at least partially covers the lens mount base 250. The gimbal base 510 is oriented such that the lens 260 is in registration with the second opening 530 and more specifically, at least a portion of the lens 260 is disposed within the second opening 530. The gimbal base 510, lens mount base 250 and substrate 200 are all disposed in at least substantially parallel relationship relative to one another. The gimbal base 510 and lens mount base 250 are out of the line of vision of the camera 400 and therefore, do not interfere with the image capturing performed by the camera 400.

The gemstone holder assembly 500 also includes a gimbal assembly 600. As is known, a gimbal is a pivoted support that allows the rotation of an object about a single axis. A set of two gimbals, one mounted on the other with pivot axes orthogonal, may be used to allow an object mounted on the innermost gimbal to remain immobile (i.e., vertical in the animation) regardless of the motion of its support. The gimbal assembly 600 is in the form of a double gimbal and more specifically, the gimbal assembly 600 includes a first gimbal 630 that represents an outer gimbal. The first gimbal 630 is a continuous structure that has a flat back wall 632 and a rounded front wall 634 and thus is generally in the form of a ring. The rounded front portion is thus generally U-shaped. The first gimbal 630 is a hollow member in that a central opening 635 is formed therein. Along the back wall 632, a notch 633 is formed (e.g., a U-shaped notch). In addition, along one side of the first gimbal 630, a first coupling member 637 is mounted to one side and protrudes outwardly therefrom and a second protrusion 639 protrudes outwardly from an outer surface of the other side of the first gimbal 630. In the illustrated embodiment, the first coupling member 637 is a hollow arm structure and the second protrusion 639 is a coupling member, such as a hollow boss, that receives a pin or shaft (or rivet) 641 that extends outwardly therefrom. As shown, the first coupling member 637 can be a separate part and can be attached to the outer surface of the side of the first gimbal 630 using fasteners. The first coupling member 637 is then coupled to the drive shaft 675 of the motor 660 for controlled movement of the first gimbal 630.

The first gimbal 630 is supported and operatively connected to a device 660 that imparts movement to the first gimbal 630. For example, the device 660 can be in the form of a motor, such as a servo motor, that provides precise control over the movement of the first gimbal 630. The device 660 is coupled and secured to the gimbal base 510. In the illustrated embodiment, a mount 670 is secured to the gimbal base 510 using fasteners or the like. The mount 670 is intended to hold the motor 660 in place proximate the second opening 530 to allow a drive shaft 675 to be connected between the motor 660 and the outer gimbal 630. The illustrated mount 670 is a U-shaped bracket that opens upwardly.

More specifically, the drive shaft 675 couples to the first coupling member 637 such that the first gimbal 630 pivot about a first axis that extends through the first coupling member 637 and the drive shaft 675 and the pin 641 that is formed directly opposite the first coupling member 637. The first and second members 637, 639 thus are structures that allow the first gimbal 630 to pivot between the motor 660 and a gimbal bearing 680 that is located across the second opening 530 and is mounted to the gimbal base 510 using fasteners or the like. The gimbal bearing 680 receives the pin 641. Thus, under the driving action of the motor 660, the first gimbal 630 rotates about the first axis.

The gimbal assembly 600 also includes a second gimbal 700 that represents an inner gimbal. The second gimbal 700 is configured to rest within the hollow interior space of the first gimbal 630. The second gimbal 700 is generally circular in shape and is continuous and thus represents an inner ring. The second gimbal 700 has a front pin 710 that is received and rotates within a coupling member 712 that protrudes outwardly from a front of the second gimbal 700. The second gimbal 700 includes a coupling member 720 that is attached to a rear section of the second gimbal 700. The coupling member 720 can be a separate member that is attached to the rear section of the second gimbal 700. The coupling member 720 is configured to mate and couple the second gimbal 700 to a device 730 that imparts movement to the second gimbal 700. For example, the device 730 can be in the form of a motor, such as a servo motor, that provides precise control over the movement of the first gimbal 630. The coupling member 720 includes a hollow arm structure 725 that receives a drive shaft 740 that is operatively connected to the device 730. The operation of the device 730 imparts pivoting movement to the second gimbal 700 through the drive shaft 740 and the coupling member 720.

When the first and second gimbals 630, 700 are coupled together, the pin 710 of the second gimbal 700 is received within a recess 639 formed in the front of the first gimbal 600. The pin 710 thus pivots within the recess 639. The hollow arm structure 725 extends through the notch 633 formed in the first gimbal 600 to allow the inner second gimbal 700 to freely pivot along a second axis that extends through the drive shaft 740 and the pin 710. The pin 710 is a pivot point of the second gimbal 700.

As mentioned above, the first and second pivot axes are orthogonal to one another as is custom in a double gimbal design.

The inner second gimbal 700 supports and holds a transparent plate 750 that in turn receives and supports the gemstone on an outer facing surface thereof. The transparent plate 750 can be a glass disk as shown. The center of the transparent plate 750 is axially aligned with the laser 220 resulting in the light beam 222 being centrally focused relative to the transparent plate 750. As shown in the figures, the gemstone is disposed on the transparent plate 750 in a table down orientation. To ensure proper operation, the gemstone should be disposed initially in a central location of the transparent plate 750.

Figure 10:
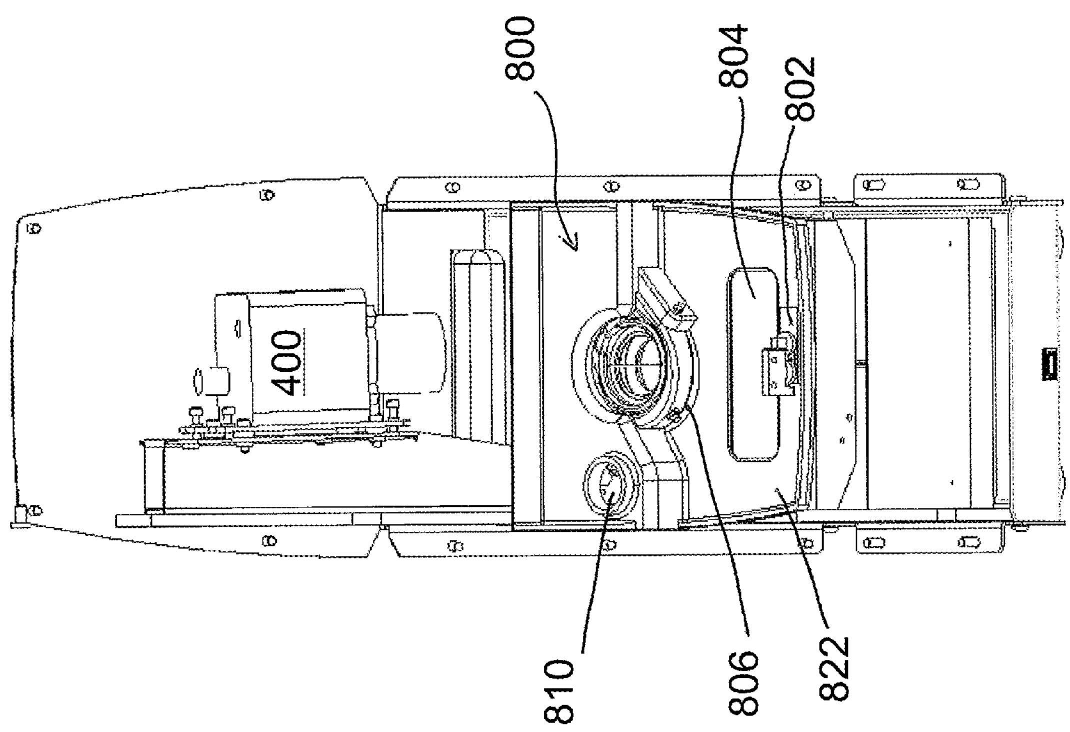
FIG. 10 is top and front perspective view of the gimbal assembly and other components.

A gimbal cover 800 is provided to cover some of the working components of the gimbal assembly. As shown in FIG. 10, the gimbal cover 800 is a multi-level body in that the cover 800 includes a lower platform 822 at a front portion of the cover 800 and an upper platform 820 at a rear portion of the cover 800 that is elevated relative to the lower platform 822. A shoulder, such as a right angle shoulder, can be formed between the platforms 822, 820. The lower platform 822 includes a first opening 802 formed therein proximate a front edge of the cover 800 and a second opening 804 adjacent the first opening 802 but spaced further from the front edge. The first opening 802 can be part of a lid latch mechanism for securely locking the lid in place. The second opening 804 is larger than the first opening 802 and is in registration with the opening 520 when the cover 800 mates with the gimbal base 510. The cover 800 also includes a third opening 806 formed therein. The third opening 806 is located both within platforms 820, 822. The third opening 806 is in registration with the opening 530. Along the platform 820, a hollow boss structure 810 with a through hole is formed. The hollow boss 810 is located proximate the third opening 806. In the illustrated embodiment, the hollow boss 810 has a circular shape.

The cover 800 is attached to the gimbal base 510 using conventional techniques, such as fasteners, such as screws.

Figure 11:
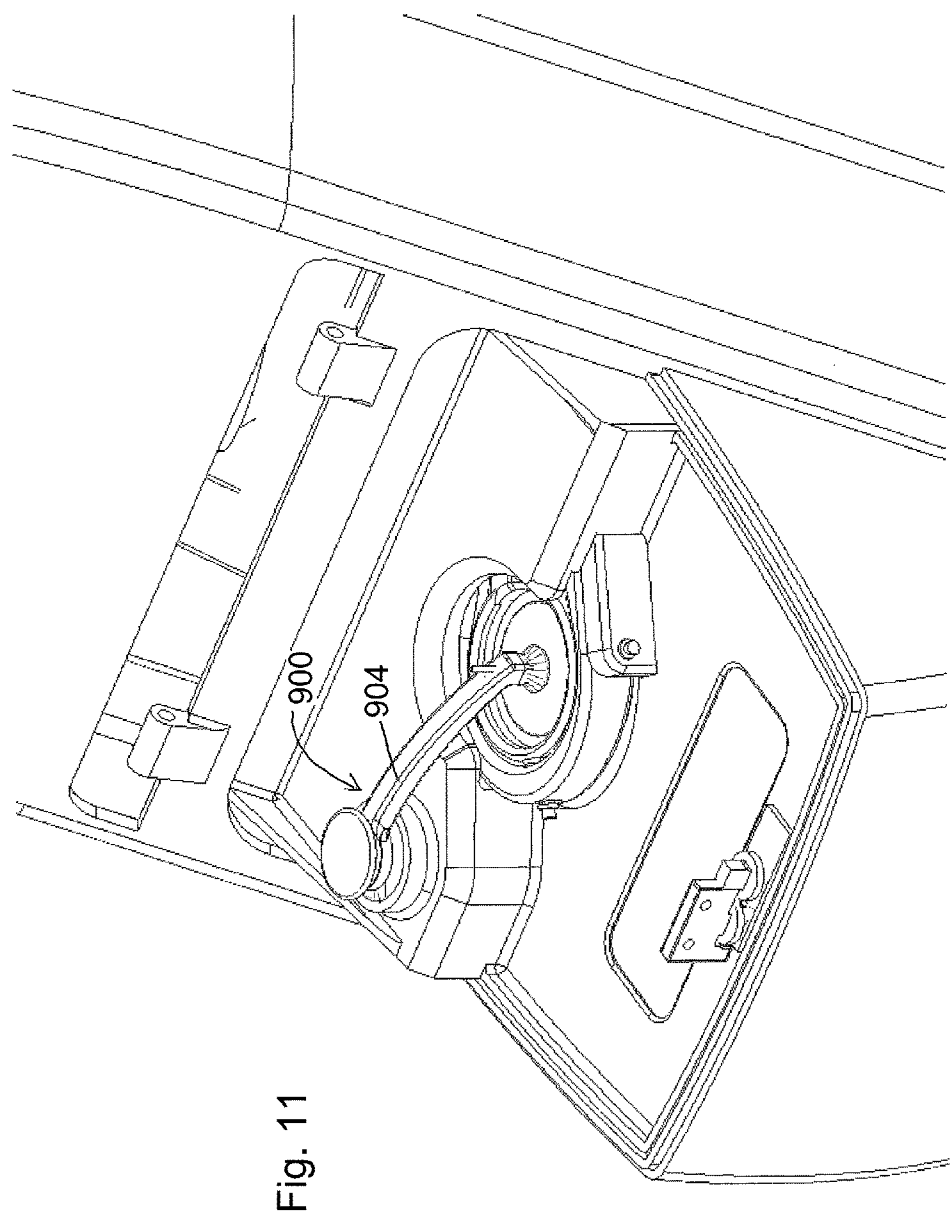
FIG. 11 shows a centering mechanism.
Figure 12:
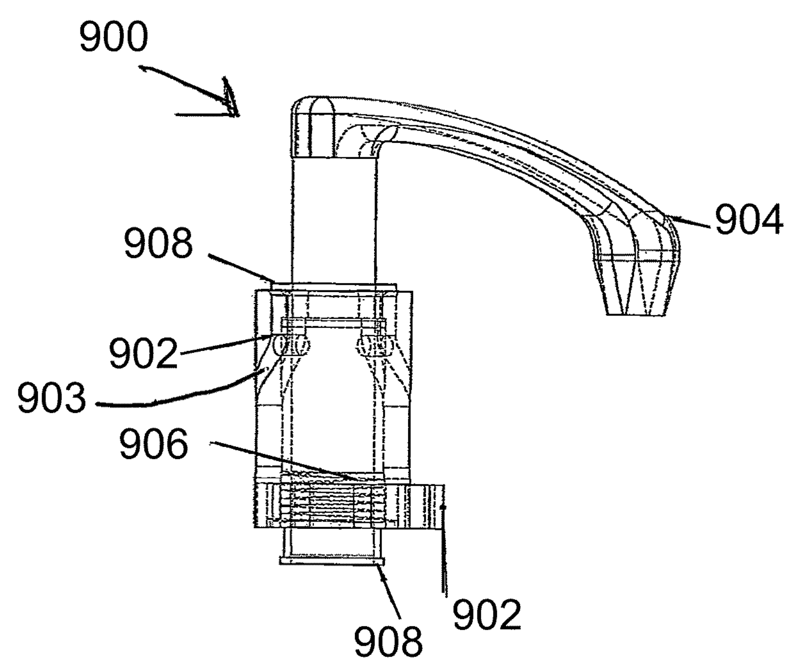
FIG. 12 is a side elevation of an adjustable plunger of the centering mechanism.

The device 100 also further includes a gemstone centering mechanism 900 shown in FIGS. 11-12. In the illustrated embodiment, the centering mechanism 900 is a manual mechanism. The gemstone centering mechanism 900 mates with the gimbal base 510 and in particular the centering mechanism 900 is disposed proximate the opening 530. The centering mechanism 900 thus seats flush against the gimbal base 510 and extends upwardly therefrom. The centering mechanism 900 is constructed to apply a centering force to a gemstone that is seating on the transparent plate 750. This centering force corrects some misalignment of the gemstone on the transparent plate 750 and ensures that the gemstone is placed directly in the center of the plate 750 and is thus axially aligned with the light beam 222 of the laser 220. This centering ensures that the optical pattern is properly generated and recorded due to the optimal positioning of the gemstone on the plate 750 (plastic or glass plate).

The centering mechanism 900 includes an outer body 902 that includes a slot or groove formed therein. The outer body 902 is thus a hollow structure and the slot extends completely through the outer body 902 and is open at least along the top end of the body 902. The outer body 902 stands upright on the gimbal base 510. The slot is non-linear in nature and is generally S-shaped or the like.

The slot/groove is part of a pin and groove arrangement and more specifically, the centering mechanism 900 includes an inner body 908 that is received within the hollow interior of the outer body 902. The inner body 908 has a height greater than the height of the outer body 902 and thus an upper section of the inner body 908 extends above the top edge of the outer body 908. The inner body 908 is rotatable within the hollow interior of the outer body 908 and in the illustrated embodiment, the inner body 908 has a cylindrical shape that complements the cylindrical shape of the hollow interior of the outer body 908. The inner body 908 has a pin that extends outwardly therefrom. The pin is constructed and is received within the slot formed in the outer body 902. It will be appreciated that the construction of the slot imparts a rotation to the inner body 908 as the inner body 908 moves linearly within the outer body 902. As discussed in more detail below, when the inner body 908 is pushed downward within the outer body 902, the pin rides within the slot toward the bottom thereof and the non-linear shape of the slot causes the inner body 908 to rotate within the outer body 902.

The gimbal base 510 includes a through opening below the centering mechanism 900 to allow the inner body 908 to extend below the gimbal base 510 in certain positions. The outer body 902 does not extend through this opening and thus seats on the top surface of the gimbal base 510.

The centering mechanism 900 also includes a biasing member 906 that is disposed within the outer body 902 and in particular is disposed below the pin of the inner body 908 and a bottom portion of the outer body 902. The biasing member 906 which can be in the form of a spring is thus held in place between the pin and the bottom portion of the outer body. The biasing member 906 is thus disposed about (surrounding relationship) the inner body 908. In a normal rest position of the biasing member 906, the biasing member 906 applies a force and positions the pin of the inner body 908 in an up position within the slot of the outer body 902.

At the top of the inner body 908, a plunger 904 is provided. The plunger 904 is generally hook shaped and extends radially outward from the inner body 908 and has an arcuate shape and terminates in a distal tip that serves as a centering tip. More specifically, the centering tip is shaped to mate with a cut gemstone that is lying with its table on the transparent plate 750.

The plunger 904 moves between an up position (rest position) and a down position (actuated position). In the up position, the plunger 904 is not in registration with the transparent plate 750 at least relative to the central portion thereof. In other words, the plunger 904 is offset from the transparent plate 750 and from the gemstone thereon. The up position of the plunger 904 corresponds to the up position of the pin and the rest position of the biasing member 906.

In the down position, the plunger 904 moves downwardly due to a downward force being applied thereto and since the plunger 904 is connected to the inner body 908, the downward movement of the inner body 908 within the outer body 902 causes a rotation of the inner body 908 and the plunger 904 due to the pin moving within the slot. As the pin moves downwardly within the slot, the plunger 904 not only moves downward but it also rotates so as to cause the centering tip thereof to pivot into rotation and be in registration with the center of the transparent plate 750 and thus be in registration with the gemstone and come into contact therewith. This controlled movement of the plunger 904 thus applies a centering force to the gemstone since the centering tip of the plunger is shaped to capture and hold the gemstone and thus as the plunger 904 moves into the down position which represents the centered gemstone position, the plunger 904 makes any incremental adjustment that is needed to cause the gemstone to be centered on the transparent plate 750 and be in axial alignment with the light beam 222. Thus, the centering mechanism 900 ensures that the gemstone is properly positioned on the transparent plate 750 and is in axial alignment with the light beam 222.

As the plunger 904 and inner body 908 move downward, the biasing member 906 stores energy (compresses) and thus an automatic return force is generated. Thus, when the plunger 904 is released after the registration process is completed, the inner body 908 and plunger 904 automatically move upward back to the up position which is the rest position and the plunger 904 is spaced away from the light beam 222 and the gemstone can be easily removed from the transparent table 750.

It will be appreciated that the curved portion of the slot causes the rotation of the plunger 904 and then after rotation, the pin rides within a lower linear section which is translated into a linear downward movement of the plunger 904. Thus, the curved portion of the slot causes the rotation of the plunger 904 into a position where the centering tip is axially aligned with the light beam (FIG. 26) but can be spaced directly above and not in contact with the gemstone. Continued movement of the plunger 904 in a downward direction causes the pin to move in the lower linear section and this is translated into the centering tip moving linearly downward into contact with the gemstone. This lower linear section thus accommodates different sized stones since the degree that the plunger 904 needs to move downward into contact with the gemstone depends upon the size and shape of the gemstone.

In yet another embodiment, the gemstone centering mechanism 900 can be an automated process. In other words, the movement of the plunger 904 between the up and down positions can be automated as by operatively connecting the plunger 904 to a motor or the like, such as a servo motor, that controllably drives the plunger 904 between the two positions based on user commands.

Accordingly, the centering mechanism 900 can comprise an automated centering system that includes a movable plunger that moves between a first position in which the plunger is spaced from the gemstone and from a center region of the platform and a second position in which a centering tip of the plunger is at least substantially axially aligned with the beam of light 222. The centering mechanism 900 is operatively connected to a device (e.g., servo motor) that automatically moves the plunger between the first and second positions. In yet another aspect, the movement of the plunger can be controlled in view of at least one inputted gemstone characteristic. For example, prior to the registration process, the user can input characteristics concerning the gemstone, such as the shape and size of the gemstone. The plunger can then be driven into proper position for centering the gemstone in view of this inputted information since the plunger should come into contact and move the gemstone to the centered position but at the same time, the plunger should not drive the gemstone into hard engagement with the platform 750.

In yet another aspect, the centering tip can include a sensor for sensing contact with the gemstone. The movement of the plunger is stopped when contact with the gemstone is sensed and the centering tip is in the centered position. For example, the sensor can be an optical sensor that senses contact between the centering tip and the gemstone. A signal can be sent to a controller (processor) for controlling movement of the plunger.

In the fully assembled position, the inner body 908 and the plunger 904 extend through the hollow boss 810 of the gimbal cover 800.

In yet another aspect, the present invention is part of a computer system that can include a video frame grabber card and associated software, memory storage, a display screen, a user interface (keyboard or touch pad, etc.), image processing software and a counter. Associated with the personal computer is the printer which prints gemstone certificates. In addition, the personal computer includes communication software that permits the computer to communicate over a network with other devices, such as a wired or wireless connection.

The counter is used to maintain a check on optical images recorded in the database and is indexed for each recordal. This count is also kept with the database whereby departures in the sequence can be identified and investigated.

The following detailed description is directed to systems and methods for gemstone registration by generating an optical fingerprint of the gemstone. The referenced systems and methods are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods. Accordingly, aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather are to provide an understandable description of the systems and methods.

Figure 26:
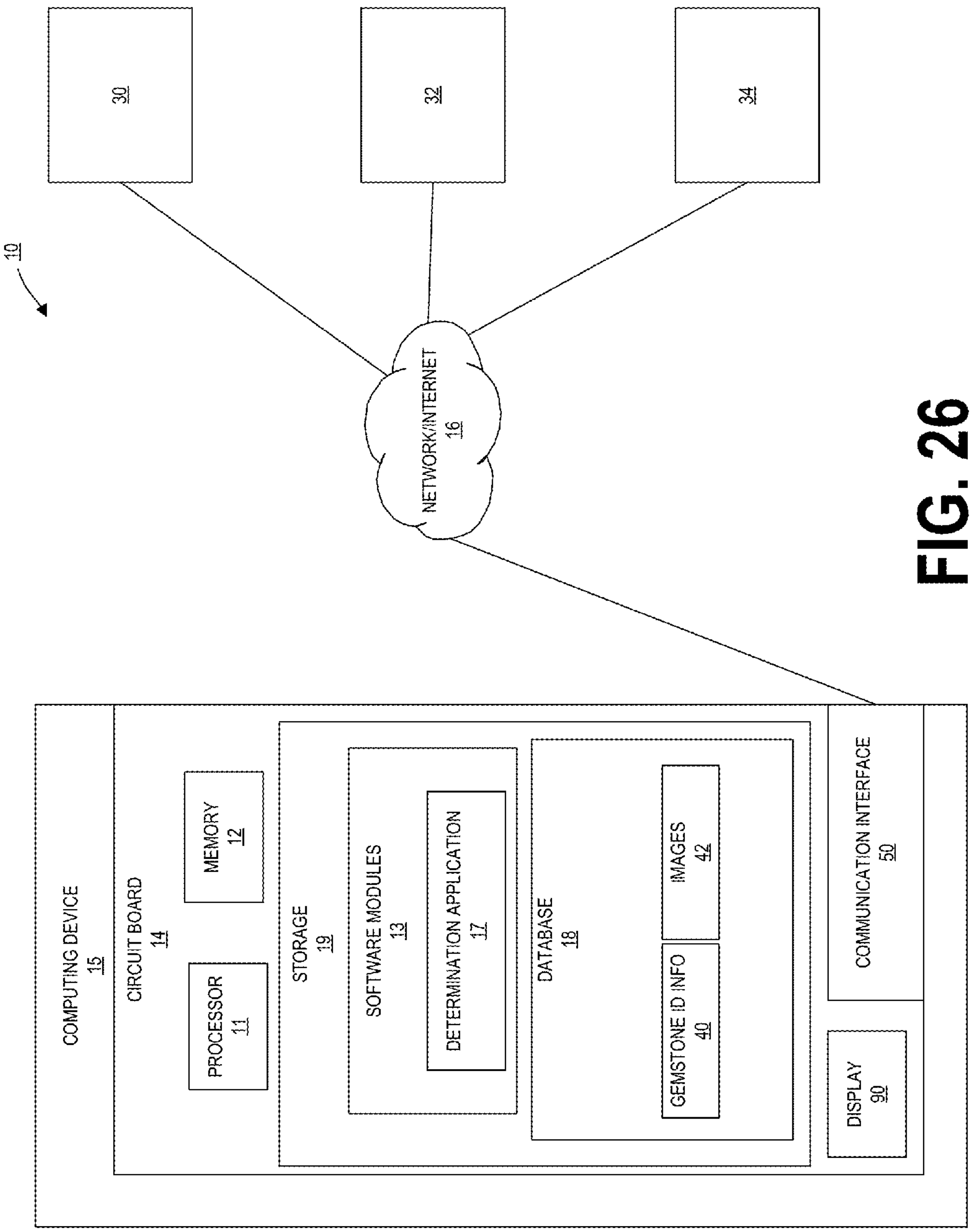
FIG. 26 is block diagram of components of an exemplary computer system.

An exemplary computer system is shown as a block diagram in FIG. 26 which is a high-level diagram illustrating an exemplary configuration of a gemstone registration system 10 that utilizes device 100. In one implementation, computing device 15 can be a personal computer or server. In other implementations, computing device 15 can be a tablet computer, a laptop computer, or a mobile device/smartphone, though it should be understood that computing device 15 of gemstone registration system 10 can be practically any computing device and/or data processing apparatus capable of embodying the systems and/or methods described herein.

Computing device 15 of gemstone registration system 10 includes a circuit board 14, such as a motherboard, which is operatively connected to various hardware and software components that serve to enable operation of the gemstone registration system 10. The circuit board 14 is operatively connected to a processor 11 and a memory 12. Processor 11 serves to execute instructions for software that can be loaded into memory 12. Processor 11 can be a number of processors, a multi-processor core, or some other type of processor, depending on the particular implementation. Further, processor 11 can be implemented using a number of heterogeneous processor systems in which a main processor is present with secondary processors on a single chip. As another illustrative example, processor 11 can be a symmetric multi-processor system containing multiple processors of the same type.

Preferably, memory 12 and/or storage 19 are accessible by processor 11, thereby enabling processor 11 to receive and execute instructions stored on memory 12 and/or on storage 19. Memory 12 can be, for example, a random access memory (RAM) or any other suitable volatile or non-volatile computer readable storage medium. In addition, memory 12 can be fixed or removable. Storage 19 can take various forms, depending on the particular implementation. For example, storage 19 can contain one or more components or devices such as a hard drive, a flash memory, a rewritable optical disk, a rewritable magnetic tape, or some combination of the above. Storage 19 also can be fixed or removable.

One or more software modules 13 are encoded in storage 190 and/or in memory 12. The software modules 13 can comprise one or more software programs or applications having computer program code or a set of instructions executed in processor 11. Such computer program code or instructions for carrying out operations for aspects of the systems and methods disclosed herein can be written in any combination of one or more programming languages, including an object oriented programming language such as Java, Smalltalk, C++, Python, and JavaScript or the like and conventional procedural programming languages, such as the “C” programming language or similar programming languages. The program code can execute entirely on computing device 15, partly on computing device 15, as a stand-alone software package, partly on computing device 15 and partly on a remote computer/device, or entirely on the remote computer/device or server. In the latter scenario, the remote computer can be connected to computing device 15 through any type of network, including a local area network (LAN) or a wide area network (WAN), or the connection can be made to an external computer (for example, through the Internet 16 using an Internet Service Provider).

One or more software modules 13, including program code/instructions, are located in a functional form on one or more computer readable storage devices (such as memory 12 and/or storage 19) that can be selectively removable. The software modules 13 can be loaded onto or transferred to computing device 15 for execution by processor 11. It can also be said that the program code of software modules 13 and one or more computer readable storage devices (such as memory 12 and/or storage 19) form a computer program product that can be manufactured and/or distributed in accordance with the present invention, as is known to those of ordinary skill in the art.

It should be understood that in some illustrative embodiments, one or more of software modules 13 can be downloaded over a network to storage 19 from another device or system via communication interface 15 for use within gemstone registration system 10. For instance, program code stored in a computer readable storage device in a server can be downloaded over a network from the server to gemstone registration system 10.

Preferably, included among the software modules 13 is a gemstone alignment application 17 that is executed by processor 11. During execution of the software modules 13, and specifically the gemstone alignment application 17, the processor 11 configures the circuit board 14 to perform various operations relating to product arrangement determination with computing device 15, as will be described in greater detail below. It should be understood that while software modules 13 and/or gemstone alignment application 17 can be embodied in any number of computer executable formats, in certain implementations software modules 13 and/or gemstone alignment application 17 comprise one or more applications that are configured to be executed at computing device 15 in conjunction with one or more applications or ‘apps’ executing at remote devices, such as computing device(s) 30, 32, and/or 34 and/or one or more viewers such as internet browsers and/or proprietary applications. Furthermore, in certain implementations, software modules 13 and/or gemstone alignment application 17 can be configured to execute at the request or selection of a user of one of computing devices 30, 32, and/or 34 (or any other such user having the ability to execute a program in relation to computing device 15, such as a network administrator), while in other implementations computing device 15 can be configured to automatically execute software modules 13 and/or gemstone alignment application 17, without requiring an affirmative request to execute. It should also be noted that while FIG. 26 depicts memory 12 oriented on circuit board 14, in an alternate arrangement, memory 12 can be operatively connected to the circuit board 14. In addition, it should be noted that other information and/or data relevant to the operation of the present systems and methods (such as database 18) can also be stored on storage 19, as will be discussed in greater detail below.

Also preferably stored on storage 19 is database 18. As will be described in greater detail below, database 18 contains and/or maintains various data items and elements that are utilized throughout the various operations of gemstone registration system 10, including but not limited to gemstone identification information 40, images 42, etc., as will be described in greater detail herein. It should be noted that although database 18 is depicted as being configured locally to computing device 15, in certain implementations database 18 and/or various of the data elements stored therein can be located remotely (such as on a remote device or server—not shown) and connected to computing device 15 through network 16, in a manner known to those of ordinary skill in the art.

Communication interface 50 is also operatively connected to circuit board 14. Communication interface 50 can be any interface that enables communication between the computing device 15 and external devices, machines and/or elements. Preferably, communication interface 50 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting computing device 15 to other computing devices and/or communication networks such as private networks and the Internet. Such connections can include a wired connection or a wireless connection (e.g. using the 802.11 standard) though it should be understood that communication interface 50 can be practically any interface that enables communication to/from the circuit board 14.

In the description that follows, certain embodiments and/or arrangements are described with reference to acts and symbolic representations of operations that are performed by one or more devices, such as the gemstone registration system 10 of FIG. 26. As such, it will be understood that such acts and operations, which are at times referred to as being computer-executed or computer-implemented, include the manipulation by processor 11 of electrical signals representing data in a structured form. This manipulation transforms the data and/or maintains them at locations in the memory system of the computer (such as memory 12 and/or storage 19), which reconfigures and/or otherwise alters the operation of the system in a manner understood by those skilled in the art. The data structures in which data are maintained are physical locations of the memory that have particular properties defined by the format of the data. However, while an embodiment is being described in the foregoing context, it is not meant to provide architectural limitations to the manner in which different embodiments can be implemented. The different illustrative embodiments can be implemented in a system including components in addition to or in place of those illustrated for the gemstone registration system 10. Other components shown in FIG. 26 can be varied from the illustrative examples shown. The different embodiments can be implemented using any hardware device or system capable of running program code. In another illustrative example, gemstone registration system 10 can take the form of a hardware unit that has circuits that are manufactured or configured for a particular use. This type of hardware can perform operations without needing program code to be loaded into a memory from a computer readable storage device to be configured to perform the operations.

For example, computing device 15 can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules 13 can be omitted because the processes for the different embodiments are implemented in a hardware unit.

In still another illustrative example, computing device 15 can be implemented using a combination of processors found in computers and hardware units. Processor 11 can have a number of hardware units and a number of processors that are configured to execute software modules 13. In this example, some of the processors can be implemented in the number of hardware units, while other processors can be implemented in the number of processors.

In another example, a bus system can be implemented and can be comprised of one or more buses, such as a system bus or an input/output bus. Of course, the bus system can be implemented using any suitable type of architecture that provides for a transfer of data between different components or devices attached to the bus system. Additionally, communications interface 50 can include one or more devices used to transmit and receive data, such as a modem or a network adapter.

Embodiments and/or arrangements can be described in a general context of computer-executable instructions, such as program modules, being executed by a computer. Generally, program modules include routines, programs, objects, components, data structures, etc., that perform particular tasks or implement particular abstract data types.

It should be further understood that while the various computing devices and machines referenced herein, including but not limited to computing device 15, computing devices 30, 32, and 34 are referred to herein as individual/single devices and/or machines, in certain implementations the referenced devices and machines, and their associated and/or accompanying operations, features, and/or functionalities can be arranged or otherwise employed across any number of devices and/or machines, such as over a network connection, as is known to those of skill in the art.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present invention need not reside on a single computer or processor, but can be distributed in a modular fashion amongst a number of different computers or processors to implement various aspects of the systems and methods disclosed herein.

Thus, illustrative embodiments and arrangements of the present systems and methods provide a computer implemented method, computer system, and computer program product for determining product arrangements. The block diagram in the figures illustrates the architecture, functionality, and operation of possible implementations of systems, methods and computer program products according to various embodiments and arrangements. In this regard, each block in the block diagram can represent a module, segment, or portion of code, which comprises one or more executable instructions for implementing the specified logical function (s). It should also be noted that, in some alternative implementations, the functions noted in the block may occur out of the order noted in the figure. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Device 100 can thus be connected to the computer system 10 using conventional means including being both wired (use of a cable) and wireless means. Data generated and recorded by the device 100 can thus be transferred to the computing device 15 that executes software (application 17). The count generated by the counter is stored in database 18.

Figure 13:
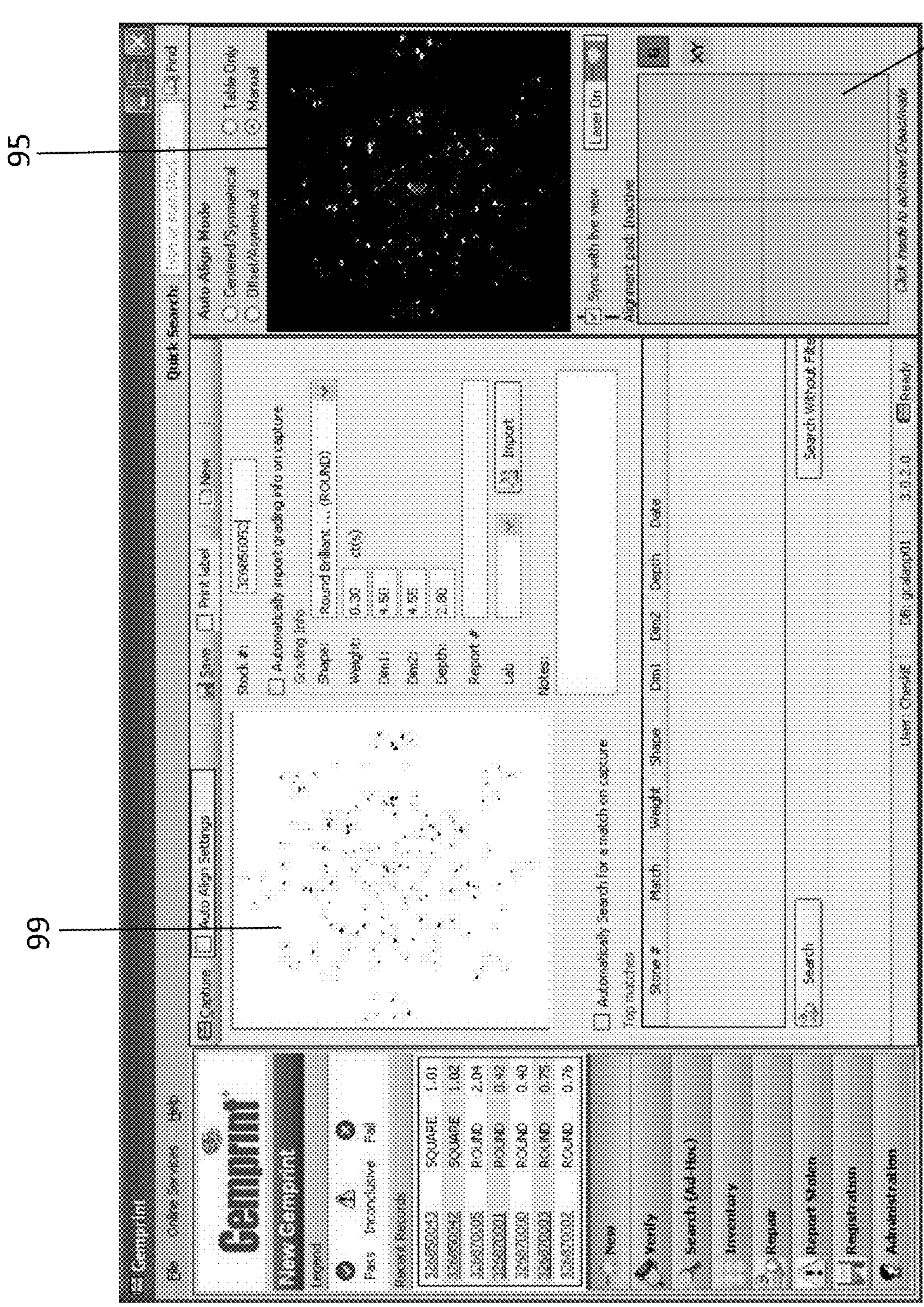
FIG. 13 is a screen shot of exemplary software for running the application.
Figure 14:
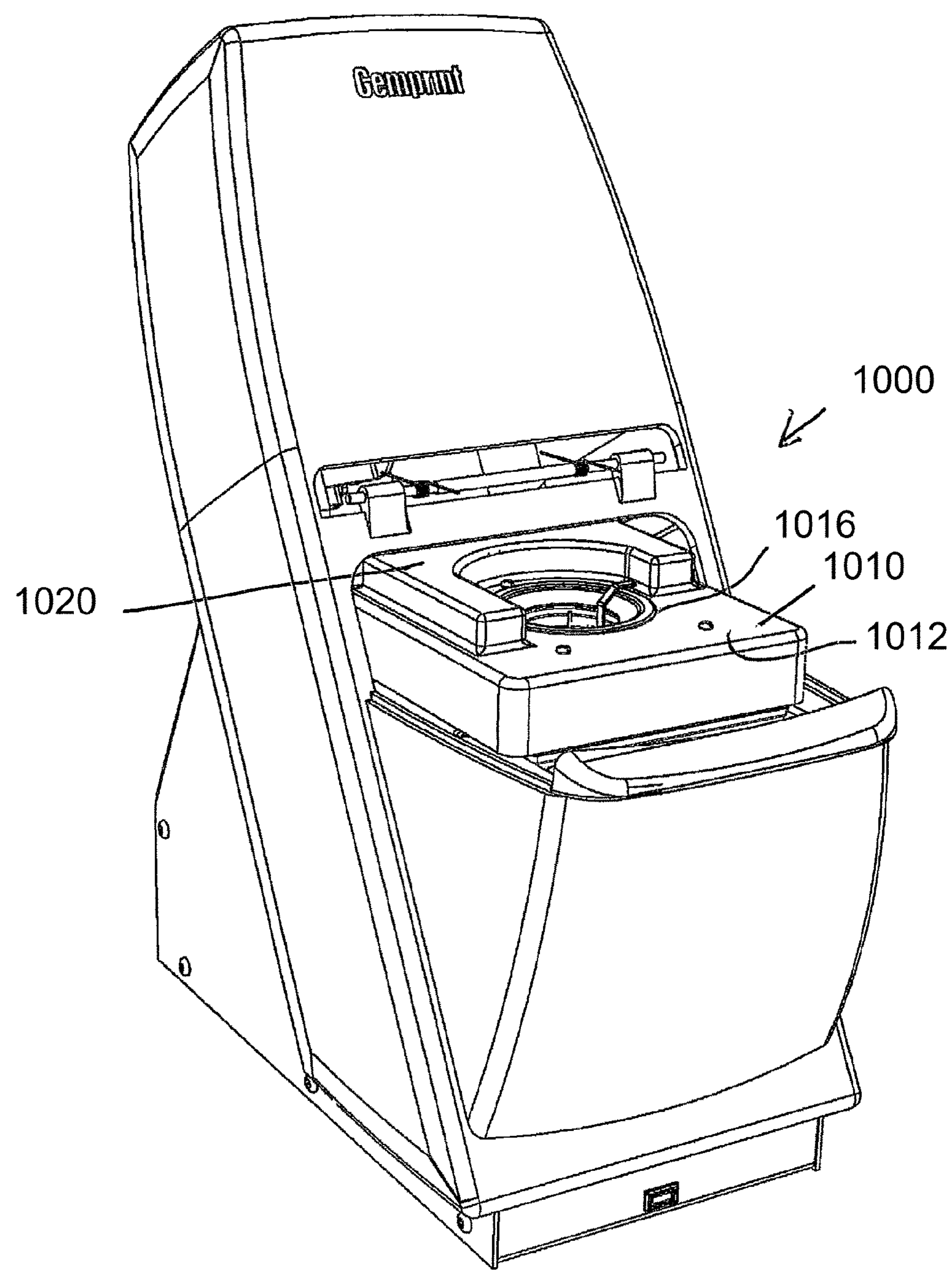
FIG. 14 is front perspective view of gem registration device according to another embodiment of the present invention with a lid removed.
Figure 15:
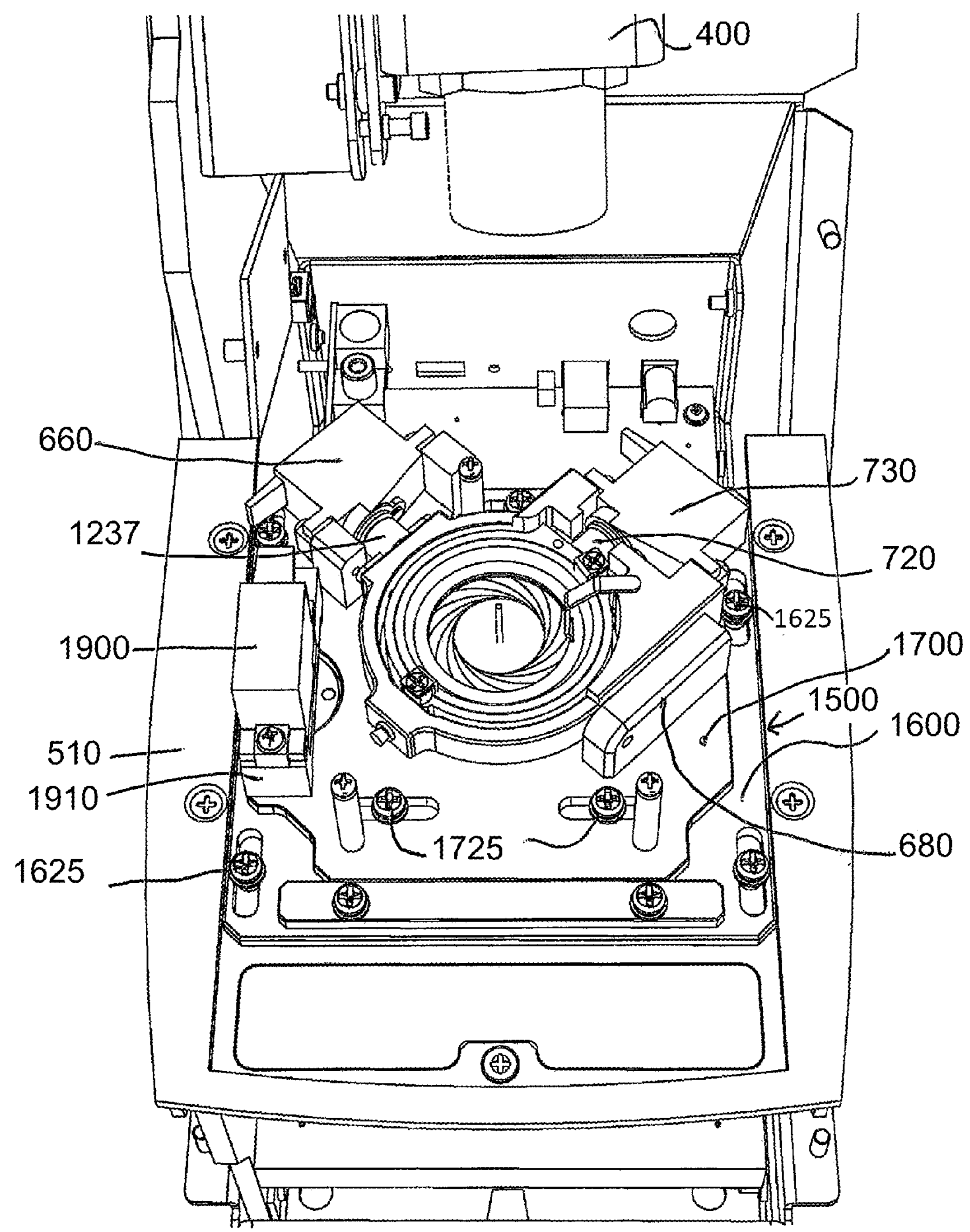
FIG. 15 is top perspective view of a gimbal assembly.
Figure 16:
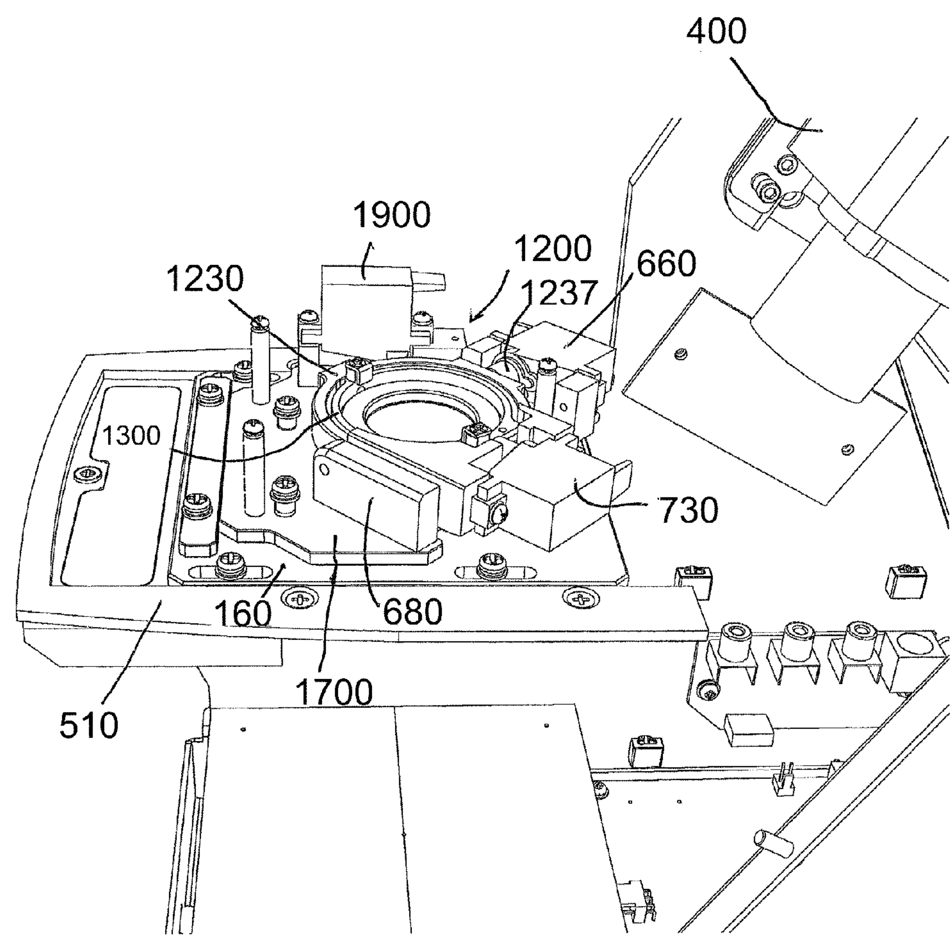
FIG. 16 is a top and side perspective view of the gimbal assembly.
Figure 17:
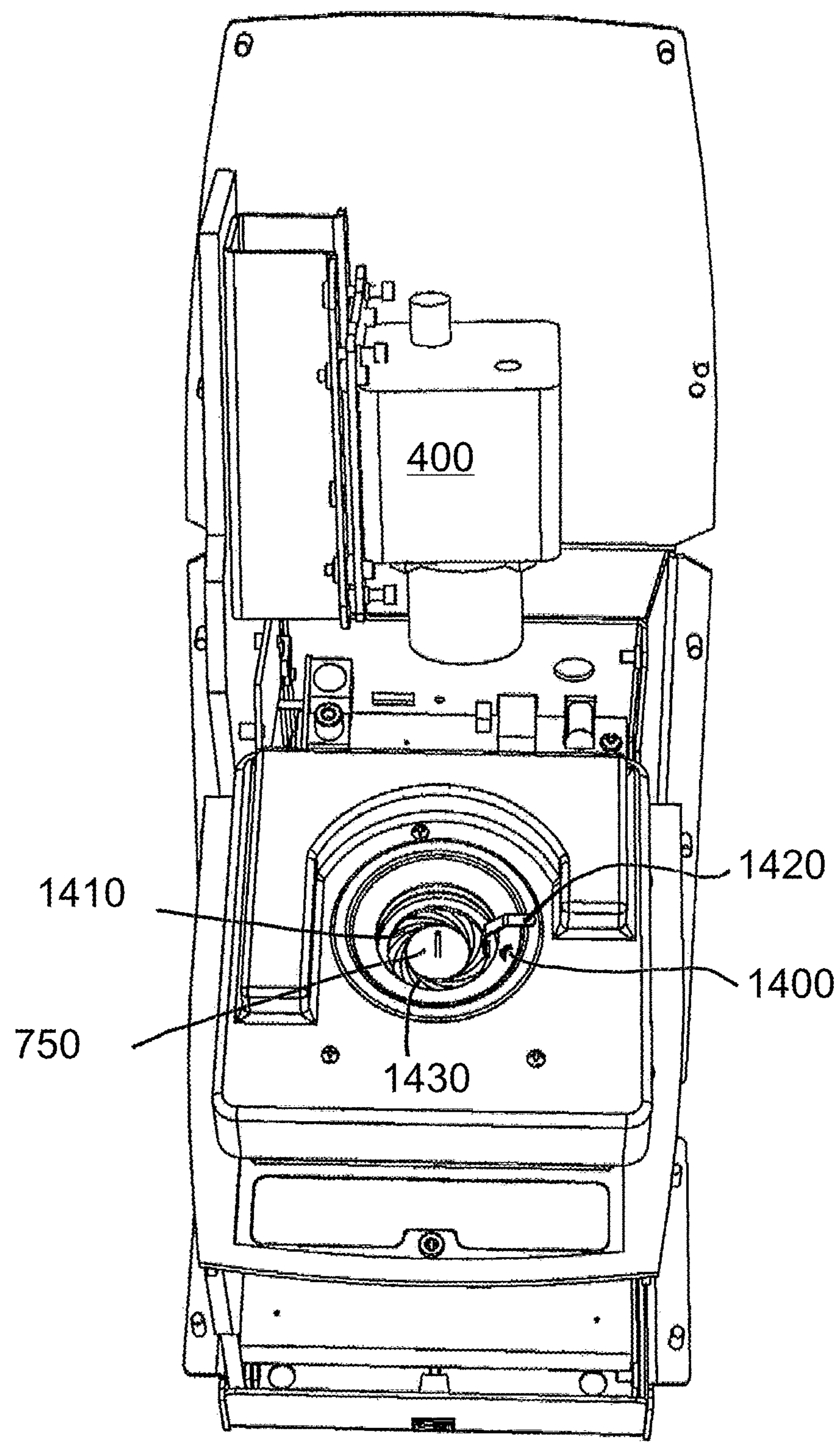
FIG. 17 is top perspective view of the gimbal assembly and a centering mechanism.
Figure 18:
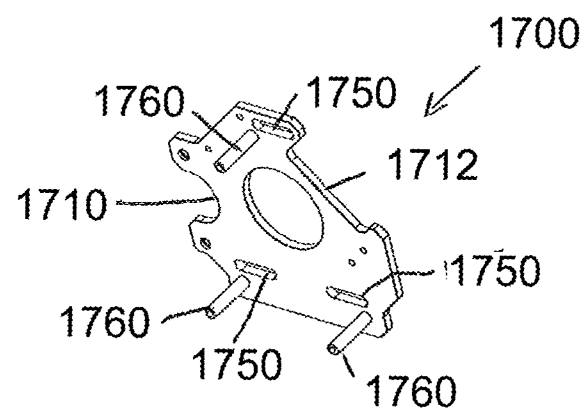
FIG. 18 is a side perspective view of a top slide plate of a centering mechanism.
Figure 19:
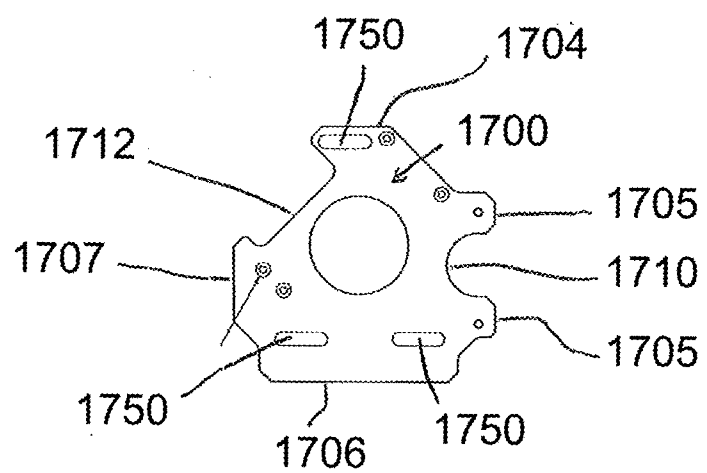
FIG. 19 is top plan view of the top slide plate.
Figure 20:
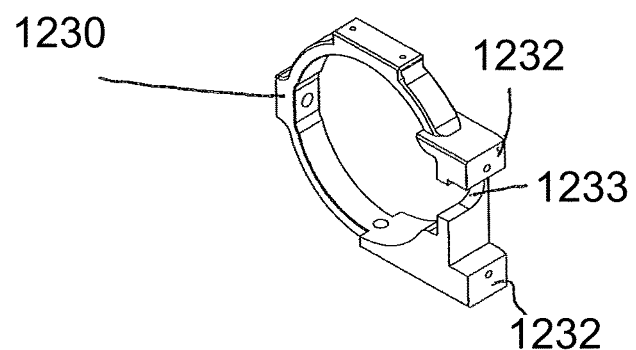
FIG. 20 is a bottom perspective view of an outer gimbal.
Figure 21:
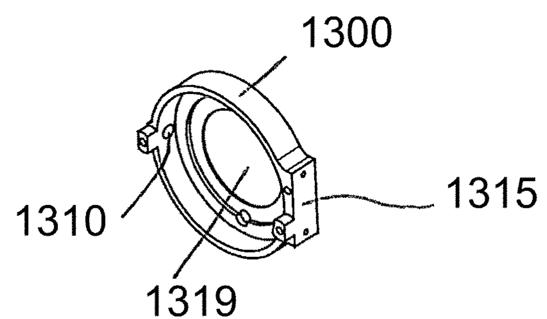
FIG. 21 is a bottom perspective view of an inner gimbal.
Figure 22:
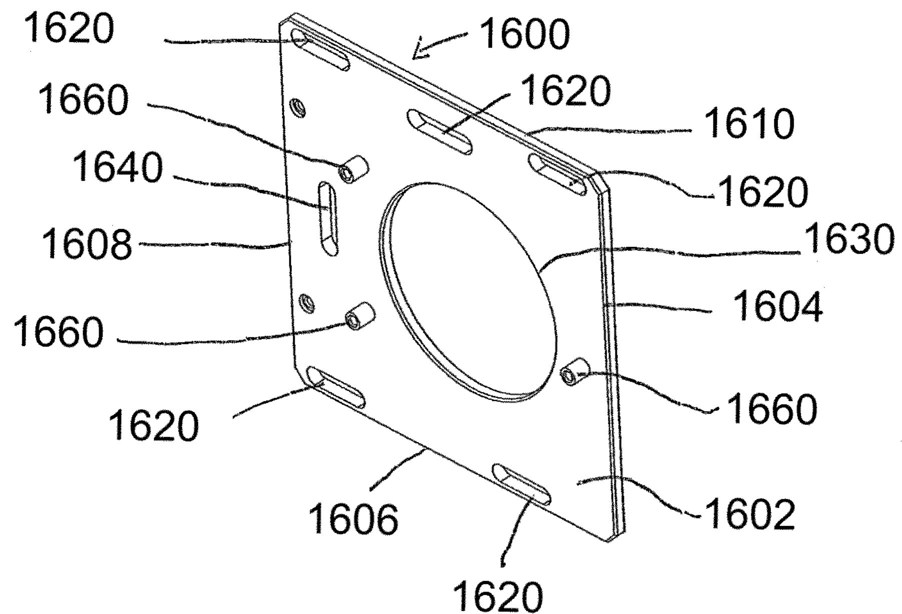
FIG. 22 is bottom perspective view of a bottom slide plate of the centering mechanism.
Figure 23:
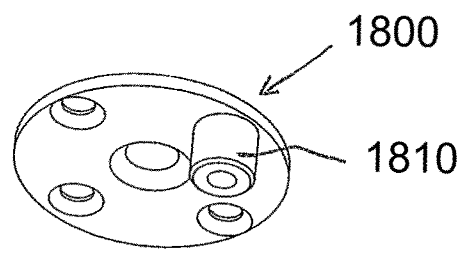
FIG. 23 is a perspective view of a driven cam member that represents a drive mechanism for each of the bottom slide plate and the top slide plate.

FIG. 13 shows one exemplary screen shot 10 of the display of the computer system. In this embodiment, the display screen is remote from the device 100 and is part of a computer system that is in communication with the device 100. However, as mentioned herein, the display screen can in other embodiments be incorporated directly into housing 110 of the device 100 itself. Additional components that are normally associated with the personal computer are also incorporated into the device 100 such as memory and processors that run software (e.g., application 18) that perform the registration process and permit wireless communication with other devices.

In the exemplary embodiment, there is a section 97 of the display screen that represents a user interface section that allows the user to easily move the gimbal assembly so as to make adjustments to the position of the gemstone and properly position the gemstone into registration (axial alignment) with the light beam 222. This is a manual mode in that the alignment is done based on commands generated by the user as by clicking different regions of the section 97 (alignment pad). For example, the user interface section can be a rectangular box that shows the centered position of the light beam 222 and shows a mark or other indicia that represents the gemstone's position on the plate 750. As discussed in applicant's other patents, the optimal alignment and the centered position of the gemstone results when the mark representing the gemstone's position is axially aligned with (in registration) with the light beam 222. A user interface tool (such as a cursor that moves in response to movement of a mouse or the like) is moved along the user interface section 12 to cause a signal to be delivered by the processor to the motors that the control the gimbal assembly. This action is thus a move and click motion in which the user can make the necessary adjustments to the position of the gemstone by moving and clicking a location on the user interface section which in turn causes the processor to send a control signal to one or more of the motors for causing movements of the gimbals that result in the gemstone's center being aligned. In other embodiment, the user interface section 12 can be a touch screen and the user can use a stylet or the like to select a position.

The gimbal assembly is thus programmed to respond to the control signals generated by the processor (which executes code) when the user moves the tool within the user interface section 12 and in particular, the precise control of one or more of the servo motors that control the inner and outer gimbals depends upon the current position of the gimbals and the location that is highlighted (clicked) in the user interface section 12. For example, only operation of the one of the servo motors may be needed to cause the proper adjustment of the gimbals which in turn provides adjustment of the gemstone's position. Alternatively, operation of both motors may be needed.

Thus, when the tool (e.g., cursor controlled by a mouse) is moved within the section 12 and then the user clicks on a specific location, the processor (which executes code) compares the present location of the gimbals compared to the newly selected position and then send controls to the servo motors to cause the necessary movement of the gimbals to position the gemstone in the newly selected position by means of movement of the gimbals, which corresponds to movement of the gemstone that is supported on the transparent support the position of which is controlled by the gimbals.

Application code can thus be embodied in any form of computer product. A computer program comprises a medium configured to store or transport computer readable code or data, or in which computer readable code or data may be embedded. Some examples of computer product include CD-ROM discs, DVD disks, ROM cards, computer hard drives, servers on a network, carrier waves, other removable media. An embodiment of the invention can be implemented as computer software in the form of computer readable code execute in a general-purpose network-enabled computing device.

It will be appreciated that the user will readily see in real time the updated position of the gemstone relative to the light beam by watching the user interface section 12 and observing movement of the mark (representing the gemstone's position) relative to the light beam. The gimbals are moved until optimal registration is realized between gemstone and light beam.

The processing software of the personal computer thus allows proper identification of the owner of the gemstone, followed by details of the gemstone as assessed by a jeweler. Details of the gemstone include the cut, clarity, colour and other characteristics. This information is keyed in using the keyboard and is stored in memory 18 (database 18). The video signal from the two-dimensional CCD camera 400 is displayed on the display screen 90 (the reflectance pattern is thus shown in real time). A scanner is actually in an enclosure, as the display of the optical response from the gemstone is dependent upon ambient conditions, such as light conditions. The jeweler conducting the gemstone identification reviews the optical response on the display screen and if he determines that the gemstone requires additional power for increased clarity, he adjusts an exposure control slide displayed on the computer screen. Adjustment of this control varies the power of the diode laser. This type of laser is easily adjustable to a host of power settings and allows the jeweler a further variable for controlling the quality of the final optical response. Too much light causes "blooming" in the video capture of the optical response and therefore less accuracy. Not enough power results in loss of low level responses from the gemstone. It is generally preferred to adjust towards a low level while maintaining the number of "hot points" in the optical response.

Other features that can be a part of the display screen are shown and described in Applicant's previous patents. For example, use of a 256 gray scale allows detection of the boundary or edges of the various points and accurately locates and sizes them. One such video image 95 is shown in FIG. 13 as it is displayed on the display screen together with the function buttons "OK", "CANCEL", "CAPTURE" and the "EXPOSURE LEVEL" slide control. The video image has "hot points" shown as white areas and the black area is the background screen. The "CAPTURE" button is used to indicate the image is suitable and should be recorded by being stored in computer memory (i.e., in a database 18 stored in memory 19) and the associated process completed.

The gemstone scanner and the personal computer 15 allow a jeweler to examine the video image of a properly located gemstone and adjusts the power of the laser by using the exposure control slide displayed on the computer screen. The jeweler thus adjusts the power of the laser to a level for optimum image capture. The video or initial image can use a 256 level gray scale and changes in exposure are immediately reflected in the displayed image. The 256 gray scale provides very good accuracy in distinguishing between areas which are reflected or refracted light beams and areas which do not have any significant light response. Once the jeweler has adjusted the device and is satisfied that the video image would be suitable for recording, he actuates the "CAPTURE" button. This CAPTURE step takes him to the next level of the program and procedure where various corrections to the image are implemented and the images have been simplified to a monochromatic display. In this case, the "hot spots" are now shown as black areas and the remaining area is white. As shown on the screen, there is a number of function buttons, namely "OK", "CANCELLED", and "CAPTURED", as well as an "EXPOSURE LEVEL" slide. This display has also undergone a number of corrections, one of which is for the angle at which the camera is located relative to the display screen. In addition, certain corrections for the LEDs and factors introduced by the particular scanner are also made. These corrections are determined upon start-up of the scanner. The LEDs produce hot spots in the image, but serve the useful purpose of locating the center of the image. During start-up, a background image is captured which includes the effect of these LEDs and other characteristics of the particular scanner and is stored. These effects can then be removed to leave a captured image more accurately reflecting the characteristics of the gemstone. It will be appreciated that the above features are merely exemplary and are not required in all applications.

Once the user presses the CAPTURE button, the static captured image is displayed at 99 and this is the image that is stored in memory and serves as the fingerprint for the gemstone.

With the images shown in FIG. 13, the jeweler then has the option to confirm that the image is appropriate for recordal and if this is the case, one would execute the CAPTURE button. This image is then combined with the inputted information regarding the identity of the owner and the various characteristics of the gemstone for recordal purposes and is stored in storage 19 (database 18). It is also possible at that time to provide a certificate of this optical display, the identity of the owner and gemstone characteristics.

Other features that can be part of the present device and the operation of the present device can be understood by a review of Applicant's previous patents that are incorporated herein.

The present system can be used by the jeweler in a number of different ways. The most simplified and common service provided by the jeweler is with respect to gemstone identification and recordal. In this case, the owner of the gemstone wishes to have the gemstone properly identified by its optical image as well as the physical characteristics of the stone and have this combined information recorded in a centralized database. In this way, the user knows that his stone has been accurately "fingerprinted" and this record is maintained in a central database for future retrieval. If the gemstone is stolen, the optical image may be transferred to a database of stolen gemstones and any recovered gemstones can be cross-checked against this database. One of the major problems is matching recovered stolen gemstones with their owner. This problem is overcome by the above arrangement where the stolen gemstone database is searchable by the police.

A further service provided by the jeweler allows verification of gemstones and can be used by the jeweler with respect to jewelry repair.

In addition, other optional functionality can be provided as part of the system. For example and as outlined herein, in contrast to the use of a diamond holder in the previous generation products, the present invention uses a moving stage with auto-alignment functionality (double gimbal assembly) that holds the stone. This present technology helps in reducing misalignments and makes the critical alignment task much easier to do. The stage can be controlled by two micro-motors (servo motors), which in turn are controlled by the user through software running on a PC, or by auto-alignment functionality in device itself or in another embodiment, as shown in FIGS. 14-23, four micro-motors can be used since the device includes (as described in detail below) an "X/Y" motorized stage that will allow for major alignment corrective actions. The oscillating stage (double gimbal) described above allows for fine "z" adjustments to correct the angle of incidence between the laser and gemstone (diamond), but the "X/Y" stage will allow for the gemstone to be physically centered above the laser. In combination with a photo cell or sensor, and the oscillating stage, the alignment can be done automatically. The platform that holds the gemstone can thus be operatively connected to one or more motor devices for controllably moving the stage (platform) in the X/Y directions. As with the fine tuning movements described herein, the adjustments of the stage in the X/Y directions can be performed using a servo motor.

In addition, multi-color fine concentric rings can be drawn or engraved on the optical glass the gemstone sits on for the initial centering step. These fixed indicia thus provide at least an initial visual indicator to assist the user in placing the gemstone on the optical glass (platform 750).

Other improvements that are realized in the present device compared to previous generation devices include the device being powered by a low voltage external power supply, replacing the 110/220 internal power supply, which helps reduce the size and the weight of the machine, and eliminates the risk of electric hazard, and the need of UL certificate. The present device also includes a new, smaller and faster microcontroller, to control the laser, LED lights, motors, and the serial communication protocol with the PC application. Other improvements concern embedding the video converter into the new machine (device 100), and connecting to the PC via a USB hub in the circuit and also eliminating the RS232-Serial connection, by adding a USB-Serial adapter to the circuit.

As mentioned above, the centering mechanism 900 utilizes a rotating plunger 904 that captures the gemstone by the culet or keel, and centers the gemstone. The plunger 904 is off-set from the stage (platform 750) and spirals as it is depressed.

In yet another embodiment, the centering mechanism can include a diaphragm mechanism that can have at least 4-6 blades and centers the gemstone by collapsing on the body of the gemstone from at least 4 directions (see FIGS. 13-24). An optional feature can be that the north-south blades/prongs come into place, and center the gemstone in one direction, be released, and the east-west blades/prongs come into place and center the gemstone in the other direction. The gemstone is thus centered in a staggered approach from two different directions.

To reduce the number of connecting cables between the device 100 and the personal computer, a USB cable can be used for to connect the device 100 to a PC. The USB cable allows serial connection to support the serial communication protocol, via an internal USB-Serial adapter and connects the internal video camera 400 to the PC via the internal video adapter. Other connections are equally possible so long as the video feed from camera 400 and data collected by device 100 is delivered to computing device 15.

An optional light beam generator can be provided in the device and is configured to project a beam down on the gemstone (diamond) so that the shadow shows up on the imaging plate (substrate 200). The shadow is then used to get dimensions and shape of the gemstone. The light source can be either a collimated (parallel beam) LED light source or a laser module with crossed line output. The crossed lines project 2 perpendicular planes of light and hit the imaging plate (substrate 200) so that they light up the X and Y axis as lines. The gemstone breaks the beam, and it is easy to find the end of the bright line where the shadow started with software that runs as a part of the device 100.

In yet another aspect, a photo cell or light sensor can be used to detect optimal alignment. Optimal alignment occurs when (1) the gemstone's table is perpendicular to the laser, and (2) the gemstone is centered in the lens. When optimal alignment occurs, this also results in the largest amount of hot spots (reflections) being displayed on the imaging plate (substrate 200). By replacing the imaging plate with a photo cell or light sensor that can detect the amount of light or reflections of light, this allows for continuous and real-time monitoring of the amount of hot spots, which thus allows the system 100 to know when optimal alignment has occurred. In this embodiment, the photocell or light sensor is in communication with the processor which in turn allows the data collected thereby to be sent to the computing device 15 for processing in accordance with application 17.

Another improvement that is part of the present device 100, as described herein, is the inclusion of a live view window 95 that allows the user to see the reflecting pattern so the user can manually adjust the stage alignment if needed (using the position control pad).

As also mentioned herein, a position control pad 97 can be part of the application. Similar to the touch pads on laptops, by using the computer mouse, the user clicks on the control pad to activate it, then, the mouse cursor automatically gets centered, and as the user moves the mouse, the stage (platform 750) either rotates on the z axis or moves left/right and up/down on the x/y axes (see below—FIGS. 14-23) to allow for manual alignment (FIG. 13). There can be a simple radio button that allows the user to switch between motor controls.

The addition of the motorized gimbal/stage mechanism (see FIGS. 13-24) results in the development of new communication protocol. This is to allow for the exchange of information between the device 100 and the present application to support the servo motors movement related commands. Exemplary software includes auto-alignment algorithms which allow the control application 17 to automatically align the gemstone once centered on the stage using the centering device. In this auto-alignment mode, the control pad 97 is not used by the user. Instead, after the centering of the gemstone is complete, the user simply presses the CAPTURE and the alignment process occurs automatically in accordance with the auto alignment application 17. In particular, the application 17 is executed and control signals are sent to the servo motors and the like to cause the parts of the device associated with the alignment process to move in a controlled manner according to discrete instructions generated by the application 17. As the position of the gemstone is moved (by movement of the support 750), the images captured by the camera 400 are continuously monitored and analyzed in terms of the reflectance pattern (captured and observed in real time) and the necessary alignment instructions (control signals) are generated by the processor based on this analysis to move the alignment components (gimbals and slide plates) of the device in the proper direction, etc., to achieve optimal alignment of the gemstone. These steps are done automatically in response to execution of code (application 17) on the computing device 15 and is driven by real time observation of the reflectance patterns as the gemstone is moved and an optimal alignment position is determined based on this analysis and processing of the captured images.

A gemstone (diamond) is properly aligned, when the hotspot (laser reflection of the diamond table), is reflected back in the center of the projection screen, which is the laser source. The mechanism consists of the following steps: detection of the hotspot/brightest spot; calculation of the distance between the detection position of the hotspot and the desired position or the center of the projection screen (also the laser source), via a translation algorithm and commanding the motors to rotate the stage to move the hotspot to the center.

As shown in FIGS. 1-24, the device 100 includes a housing 110 that contains the working components of the device 100 and provides a compact, visually pleasing product. The housing 110 is formed of a number of individual parts that are mated together to form the assembled housing 110. More particularly, the housing 110 includes a cover 120 that is formed of a first cover part 130 and a second cover part 150. The first cover part 130 represents a forward portion of the cover 120, while the second cover part 150 represents a rear portion of the cover 120.

FIGS. 13-24 disclose a gemstone registration device (system) 1000 in a fully assembled condition and in particular, the device 1000 is in the form of a device for producing an optical pattern by exposing a gemstone to a beam of light. The device 1000 is very similar to the device 100 and therefore, like elements are numbered alike. In particular, the device 1000 includes a number of the same components of the device 100 and performs many of the same operations.

Several of the major differences includes but are not limited to a different gimbal cover, different manual gem centering mechanism, an X/Y adjustment mechanism for adjusting the gemstone so as to position the gemstone such that it is physically centered about the laser, thereby resulting in the greatest number of reflections, etc.

Now turning to FIG. 13, in which device 1000 is shown and includes housing 110. One difference between the devices 100 and 1000 is the gimbal construction and in particular, a gimbal cover 1010 is used instead of the gimbal cover 800. The gimbal arrangement is essentially the same in that there are two gimbals present; however, there are structural differences between the gemstone holder assembly 500 associated with the device 100 and a gemstone holder assembly 1100 associated with device 1000.

The gemstone holder assembly 1100 also includes a gimbal assembly 1200. The illustrated gimbal assembly 1200 is in the form of a double gimbal and more specifically, the gimbal assembly 1200 includes a first gimbal 1230 that represents an outer gimbal. The first gimbal 1230 is a continuous structure that has a flat back wall 1232 and a generally rounded front wall and thus is generally in the form of a ring. The rounded front portion can include a flat portion. The first gimbal 1230 is a hollow member in that a central opening is formed therein. Along the back wall 1232, a notch 1233 is formed (e.g., a U-shaped notch). In addition, along one side of the first gimbal 1230, a first coupling member 1237 is mounted to one side and protrudes outwardly therefrom and a second protrusion protrudes outwardly from an outer surface of the other side of the first gimbal 1230. In the illustrated embodiment, the first coupling member 1237 can be the same as the member 637 and be a hollow arm structure and the second protrusion and can be like the second protrusion 639 and be a coupling member, such as a hollow boss, that receives a pin or shaft (or rivet) that extends outwardly therefrom. As shown, the first coupling member 1237 can be a separate part and can be attached to the outer surface of the side of the first gimbal 1230 using fasteners. The first coupling member 1237 is then coupled to the drive shaft of the motor 660 for controlled movement of the first gimbal 1230.

The first gimbal 1230 is supported and operatively connected to a device 660 that imparts movement to the first gimbal 1230. For example, the device 660 can be in the form of a motor, such as a servo motor, that provides precise control over the movement of the first gimbal 1230. The device 660 is coupled and secured to the gimbal base 510. A mount can be used to secure to the gimbal base 510 using fasteners or the like. The mount is intended to hold the motor 660 in place to allow a drive shaft to be connected between the motor 660 and the outer gimbal 1230. The illustrated mount can be a U-shaped bracket that opens upwardly.

As in the device 100, the first gimbal 1230 pivots about a first axis that extends through the first coupling member 1237 and the drive shaft and the pin that is formed directly opposite the first coupling member 1237. The first member 1237 and the opposite pin thus are structures that allow the first gimbal 1230 to pivot between the motor 660 and a gimbal bearing 680. The gimbal bearing 680 receives the pin located opposite the first member 1237. Thus, under the driving action of the motor 660, the first gimbal 1230 rotates about the first axis.

The gimbal assembly 1200 also includes a second gimbal 1300 that represents an inner gimbal. The second gimbal 1300 is configured to rest within the hollow interior space of the first gimbal 1230. The second gimbal 1300 is generally circular in shape and is continuous and thus represents an inner ring. The second gimbal 1300 has a front pin (not shown but similar to pin 710) that is received within hole 1310. The second gimbal 1300 includes a coupling member (e.g., coupling member 720) that is attached to a rear section 1315 of the second gimbal 1300. The coupling member can be a separate member that is attached to the rear section 1315 of the second gimbal 1300. The coupling member is configured to mate and couple the second gimbal 1300 to a device 730 that imparts movement to the second gimbal 1300. For example, the device 730 can be in the form of a motor, such as a servo motor, that provides precise control over the movement of the first gimbal 1230. The operation of the device 730 imparts pivoting movement to the second gimbal 1300 through a drive shaft and the coupling member (e.g., coupling member 720) between the second gimbal 1300 and the motor 730.

When the first and second gimbals 1230, 1300 are coupled together, the pin of the second gimbal 1300 is received within a recess formed in the front of the first gimbal 1230. The pin thus pivots within the recess. The hollow arm structure 725 extends through the notch 1233 formed in the first gimbal 1230 to allow the inner second gimbal 1300 to freely pivot along a second axis that extends through the drive shaft and the pin. This pin is a pivot point of the second gimbal 1300.

As mentioned above, the first and second pivot axes are orthogonal to one another as is custom in a double gimbal design.

The inner second gimbal 1300 supports and holds a transparent plate (e.g., plate 750) that is received in opening 1319 that in turn receives and supports the gemstone on an outer facing surface thereof. The transparent plate can be a glass disk. The center of the transparent plate is axially aligned with the laser 220 resulting in the light beam 222 being centrally focused relative to the transparent plate 750. As shown the gemstone is disposed on the transparent plate in a table down orientation. To ensure proper operation, the gemstone should be disposed initially in a central location of the transparent plate.

The gimbal cover 1010 is different than the gimbal cover 800 but serves the same purpose and is provided to cover some of the working components of the gimbal assembly. The gimbal cover 1010 is a multi-level body in that the cover 1010 includes a lower platform 1012 at a front portion of the cover 1010 and an upper platform 1020 at a rear portion of the cover 1010 that is elevated relative to the lower platform 1012. A shoulder, such as a right angle shoulder, can be formed between the platforms 1012, 1020. The lower platform 1012 can include a pair of mounting holes proximate a front edge of the cover 1010. The cover 1010 includes a main opening 1016 formed therein. The third opening 1016 is in registration with the opening 530 of the gimbal base. The cover 1010 is attached to the gimbal base using conventional techniques, such as fasteners, such as screws.

As with the device 100, the device 1000 also further includes a gemstone centering mechanism 1400. In the illustrated embodiment, the centering mechanism 1400 is a manual mechanism similar to mechanism 900. In the illustrated embodiment, the centering mechanism 1400 has an iris diaphragm construction and in particular, the mechanism 1400 is a shutter mechanism (similar to a camera) that is in the form of a circular device with a variable diameter. The mechanism 1400 utilizes a diaphragm with a top aligned disc and a lever that allows the user to control the diaphragm from above. In particular, the mechanism includes a circular body 1410 that has a hollow center. The diaphragm collapses on the body of the gemstone (jewelry (e.g. set ring) from all directions and physically centers the object on the plate 750.

Along the circular body 1410, a tab (lever) 1420 is provided. The tab 1420 is an upstanding member relative to the circular body 1410 that provides a thumb grasp for a user to allow the user to adjust the shutter. The tab 1420 is thus part of the shutter actuator and can move toward and away from the center of the circular body 1410 (defined within the hollow center of the body 1410). Thus, the user can place a thumb on the tab 1420 and slide it linearly toward the center of the body 1410 so as to collapse blade elements 1430 that are located within the center opening of the body 1410. The blade elements 1430 define a center opening (iris) that has a variable diameter depending upon the precise location of the blade elements 1430. For example, if the user pushes the tab 1420 toward the innermost location, the blade elements 1430 expand and define a center opening of minimum diameter. Conversely, when the tab 1420 is pulled radially outward to the body 1410, the blades collapse and define a center opening of maximum diameter.

The mechanism 1400 is constructed to apply a centering force to a gemstone that is seated on the transparent plate 750 to provide an initial rough alignment. This centering force corrects some misalignment of the gemstone on the transparent plate 750 and ensures that the gemstone is placed directly in the center of the plate 750 and is thus axially aligned with the light beam 222 of the laser 220. This centering ensures that the optical pattern is properly generated and recorded due to the optimal positioning of the gemstone on the plate 750 (plastic or glass plate).

The centering mechanism 1400 operates as follows. First, the user places the gemstone on the plate 750 in a generally or approximate center area or even at an off centered location. The user then moves the tab 1420 radially inward toward the gemstone, thereby causing an unfolding (expansion) of the blade elements 1430. As the blade elements 1430 unfold, the expanding blade elements 1430 contact the gemstone that rests on the plate 750 and drive the gemstone to a center location since the blade elements 1430 define a perfectly centered opening or hole. This mechanism accommodates different sizes gemstones.

In accordance with the present invention, the device 1000 advantageously includes an additional means 1500 for producing an optimal alignment for the gemstone. Just as in manual alignment, automatic optimal alignment occurs when the gemstone is physically centered about the laser, resulting in the greatest number of reflections. In the device 1000, this form of alignment is automated and more specifically, the device 1000 is an electronic computerized device. The device 1000 thus includes a processor/controller that runs on software.

As described in detail below, in order to automate this additional automated centering mechanism 1500, the software (application 17) associated with the device 1000 controls a processor which executes moves an X motor (e.g., servo motor) to a predetermined home position (e.g., a zero position) and the number of reflections of the gemstone is recorded. The X motor continues to move in multiple directions while continuing to monitor the number of reflections being produced. Once a movement results in a lesser amount of reflections, the drive pattern is reversed and descending steps are used until optimal alignment has occurred. As described herein, this process is repeated for a Y motor until optimal (automated) alignment has occurred.

Now referring to attached figures, this additional centering mechanism 1500 is illustrated. The mechanism 1500 includes a bottom slide plate 1600 that is slidingly coupled to the gimbal base 510. The bottom slide plate 1600 includes a first face 1602 that faces toward from the gimbal base 510 when the components are all assembled. The bottom slide plate 1600 also includes a first edge 1604, a second edge 1606, a third edge 1608 and fourth edge 1610. The first and third edges 1604, 1608 are opposite one another, while the second and fourth edges 1606, 1610 are opposite one another. Along the second edge 1606, a pair of elongated slots (oblong shape) 1620 are formed and similarly, along the fourth edge 1610, there are a plurality of elongated slots (oblong shape) 1620 formed therein. Along the edge 1608, a single slot 1640 is formed.

The bottom slide plate 1600 includes an opening 1630 is formed. The opening 1630 has a circular shape and underlies the gimbal assembly and the base plate that carries the gemstone.

On the first face 1602, the bottom slide plate 1600 has a plurality of upstanding posts 1660. The upstanding posts 1660 represent bosses or the like and in the illustrated embodiment, the posts 1660 are circular shaped bosses (posts). As shown, there are three posts 1660 arranged around the opening 1630 and in particular, there is a single post 1660 located between edge 1604 and opening 1630 and a pair of posts 1660 between the opening 1630 and the edge 1608. The posts 1660 are used to couple the bottom slide plate 1600 to the gimbal base 510.

As described herein below, the bottom slide plate 1600 represents the y plate and is configured to move a predetermined distance in the y-direction. For example, the slide plate 1600 is designed to move+/−a predetermined distance. The slots 1620 define the maximum y travel for the bottom slide plate 1600. Fixed guide posts 1625 are fixedly attached to the underlying gimbal base and are received within the slots 1620 and serve as guides for movement of the bottom slide plate 1600 in the y direction. In other words, when the posts 1625 reach one end of the slots 1620, the bottom slide plate 1600 has reached its end of travel in that direction (i.e., either in the +y direction or in the −y direction). The guides 1625 can be posts or fasteners, etc. that are upstanding.

In a normal home position prior to operating the x/y adjustment mechanism of the present invention, the guides 1625 are centrally located within the slots 1620.

The drive mechanism of the y plate 1600 is described below; however, it will be appreciated that any number of different types of motors can be used to controllably drive the y plate 1600 in the y direction, including but not limited to servo motors, etc.

This additional centering mechanism 1500 includes a top slide plate 1700 that has an irregular shape. The top slide plate 1700 includes a first face or surface 1702 that faces toward from the bottom slide plate 1600 and the gimbal base 510. The opposite second face of the top slide plate 1700 is the surface on which the gimbal assembly is mounted and therefore, movement of the top slide plate 1700 is imparted to movement of the table and the gemstone resting thereon relative to the fixed position laser beam.

The top slide plate 1700 includes a first edge 1704, edge 1705, edge 1706, and edge 1707, with edges 1704, 1706 being opposite one another and edges 1705, 1707 being opposite one another. The top slide plate 1700 represents the x plate and is configured to overlie and move relative to the y plate 1600. Along the edge 1705, an arcuate slot 1710 is formed. Between the edges 1704, 1707, a notch 1712 is formed.

The top slide plate 1700 includes a main central opening or hole 1730 that is in registration with the 1630 to permit the laser beam to pass through and come into contact with the gemstone that rests on the plate. As with the y plate 1600, the x plate 1700 includes a plurality of slots 1750 that limit and define the degree of x travel of the x plate 1700. Similar to the y plate, the slots 1750 of the x plate 1700 receive guide posts 1725 that serve to guide and limit the movement of the x plate 1700. In the illustrated embodiment, the posts 1725 are fixed to the underlying y plate 1600 and this allows the x plate 1700 to move in the x direction relative to the y plate 1600. There are three guide posts 1725 that are received within the slots 1750. Since the gimbal assembly is mounted to the x plate 1700, it will thus be understood that movement in the y direction of the y plate 1600 likewise causes the gimbal assembly and gemstone to move in the y direction relative to the laser beam which has a fixed position.

The slide plate 1700 is designed to move+/−a predetermined distance. The slots 1750 define the maximum y travel for the top slide plate 1700. In other words, when the posts 1725 reach one end of the slots 1750, the top slide plate 1700 has reached its end of travel in that direction (i.e., either in the +x direction or in the −x direction). The guides 1725 can be posts or fasteners, etc. that are upstanding.

In a normal home position prior to operating the x/y adjustment mechanism of the present invention, the guides 1725 are centrally located within the slots 1750.

The top slide plate 1700 also includes a plurality of upstanding coupling member 1760 that extend upwardly from the face (surface) of the top slide plate 1700 and serve as spacers or the like.

The top slide plate 1700 is also driven using any number of different drive mechanisms including but not limited to using as a motor, such as a servo motor. In the illustrated embodiment, the drive mechanism for each of the bottom slide plate 1600 and the top slide plate 1700 is in the form of a driven cam member 1800 that is operatively coupled to a motor 1900. The cam member 1800 and the motor 1900 are constructed such that the circular motion of the cam member 1800 is imparted into linear movement of the respective slide plate. The cam member 1800 is defined by a circular body that has an upstanding post 1810 which in the illustrated embodiment, the post 1810 has a circular shape. The cam member 1800 mates with the respective plate 1700, 1800, the circular motion of the cam member 1800 is translated into linear movement along the desired direction of the sliding plate. For example, with respect to the bottom slide plate 1600, the driven cam member 180 imparts linear motion along the y direction and with respect to the top slide plate 1700, the driven cam member 1800 imparts linear motion along the x direction.

In the illustrated embodiment, the motor 1900 is mounted to its supporting structure via a mount or bracket 1910. In the case of the motor 1900 that is associated with the x plate, the bracket 1910 is coupled to the plate 1700. The bracket 1910 includes a hole 1912 through which the post 1810 is received.

As shown, the post 1810 is off centered and therefore, when the post 1810 is constrained to a fixed location, the rotation of the cam member 1800 creates as eccentric driven member. At least a portion of the body of the driven member 1800 is received within the notch 1710 and depending upon the location of the driven member 1800 relative to the inner edge of the notch/slot 1710, the plate 1700 is driven a prescribed distance in the x direction. As the cam member 1800 rotates, more and more of the cam plate 1800 comes into contact with the plate 1700 and urges the plate in the respective +x direction or the −x direction.

As described herein, the cam plate 1800 and the motor 1900 can be constructed such that rotation of the cam member 1800 in one direction causes the slide plate 1700 to move a prescribed distance (e.g., up to +¼ inch), while rotation in the opposite direction causes the slide plate 1700 to move a prescribed distance in the opposite direction (e.g., up to −¼ inch). The same can be true for the y plate 1600 as described herein It will be appreciated that the use of a servo motor 1900 allows one to precisely control the movement of the y plate 1600 in small incremental steps and thus allows the plate to be moved in small incremental movements in both the plus (+) and minus (−) directions. This allows precise control over the alignment of the gemstone since the gimbal assembly is coupled to the top slide plate 1700.

The motor 1900 and cam member 1800 for the y plate 1600 is disposed beneath the y plate 1600 towards the front of the device and underneath the gimbal base 510. Thus, the same type of arrangement can be used for incrementally advancing the y plate 1600 along the y axis.

As discussed herein, the servo motors are controlled by means of a processor that sends controls signals thereto and monitors the position of the gimbals by executing software (application 17) and in response moves the gimbals.

It will therefore be appreciated that the cam member 1800 and associated motor 1900 is merely one means for driving the respective plate 1600, 1700 and other types of systems can be used for advancing the respective plate 1600, 1700 an incremental distance along the respective axis. In the present arrangement, the x plate is carried by the y plate; however, other arrangements are possible.

Figure 24:
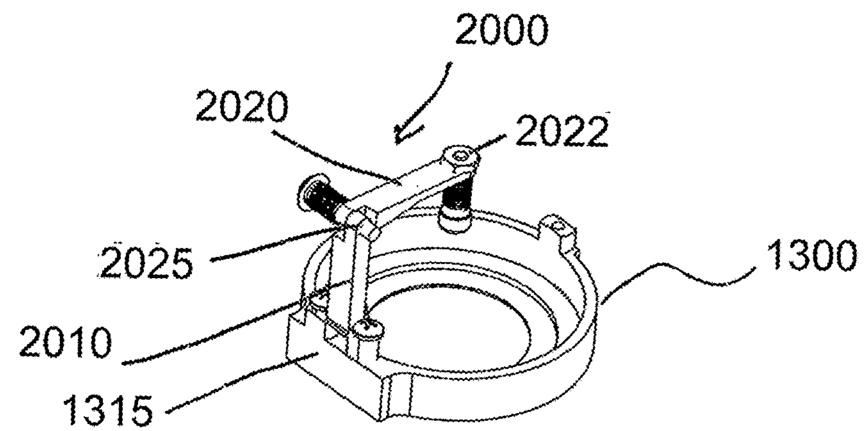
FIG. 24 is a perspective view of a gimbal extension arm for holding a jewelry article in place during the auto alignment process.
Figure 25:
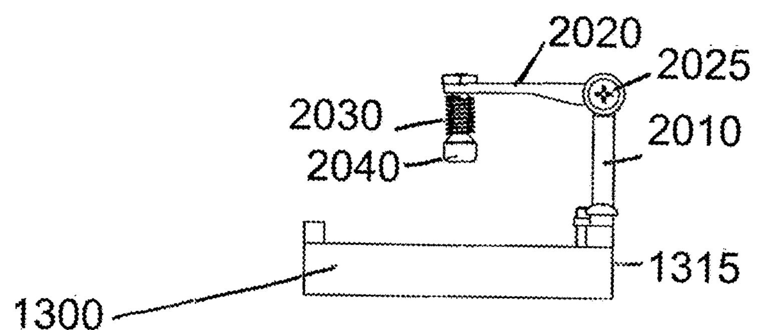
FIG. 25 is a side elevation of the gimbal extension arm.

FIGS. 24-25 show a mechanism 2000 for retaining a jewelry article while the gemstone associated therewith is centered using the centering mechanism/alignment feature described herein. This mechanism 2000 is intended for use when instead of a loose gemstone, a jewelry article, such as a ring, is placed on the transparent plate 750 that is supported by the inner gimbal 1300. The mechanism 2000 applies a retention force to the jewelry article to ensure that the jewelry article does not accidentally move during operation of the device and in particular, during the centering operation.

The mechanism 2000 includes a first support arm 2010 that is attached to and extends upwardly from the rear 1315 of the inner gimbal 1300. A second support arm (extension arm) 2020 extends from the first support arm 2010 and is movable attached thereto and in particular is pivotally attached thereto. The extension arm 2020 thus pivots about a pivot 2025. A fastener 2030, such as a screw, at the pivot 2025 to lock the extension arm 2020 relative to the first arm 2010. At the distal end 2022 of the arm 2020, a retaining (jewelry contacting) arm 2030 extends downwardly therefrom. The retaining arm 2030 is the arm that applies a force to the jewelry article for stabilizing and fixing the location of the jewelry article on the plate 750. The arm 2030 is adjustable in that it can be lowered and raised relative to the arm 2020. The adjustment can be by means of a fastener in which the arm 2030 is a threaded pin or the like that mates with a threaded opening in the arm 2020 at end 2022. Alternatively, the arm 2030 can be a spring-loaded arm that applied a force to the jewelry article that is located underneath.

The distal, free end of the arm 2030 can include a pad 2040, such a rubber pad or structure that contact and grips the jewelry article without causing damage thereto.

In accordance with the present invention, the device 1000 includes an auto-alignment feature which can be represented by a button or the like that can be selected by the user on a web page such as the ones shown on the present figures. The auto-alignment feature is based on software that runs an auto alignment algorithm (application 17) that is configured to allow the control application of the device to automatically align the gemstone once the gemstone is placed on the stage using the above described centering mechanism, such as the iris diaphragm type mechanism.

The gemstone is properly aligned, when the hotspot (laser reflection of the gemstone (e.g., diamond) table is reflected back in the center of the projection screen, which is the laser source and when the gemstone (diamond) is physically centered, resulting in the maximum amount of reflections. The centering process executed by application 17 consists of multiple steps: (1) detection of the hotspot/brightest spot; (2) calculation of the distance between the detection position of the hotspot and the desired position or the center of the projection screen (also the laser source) via a translational algorithm; (3) commanding the motors to rotate the stage to move the hotspot to the center; and (4) once this alignment has occurred, the x/y motors are commanded to move in small steps, which the software uses image recognition to continuously determine the number of hotspots until optimal alignment is achieved.

The critical reference point for the auto-alignment is the correct identification of the reflection of the table of the diamond. This needs to be done by analyzing the captured images (of the hotspots) by means of the device's software that is executed by computing device 15. The table of the gemstone (diamond) is known to produce the brightest hotspots among all of the hotspots creating the gemstone image. This is accomplished by rotating the stage in set number of predetermined (established) positions and analyzing each image to calculate reflections, angles and the distance of all potential table reflections. Once a specific member of threshold criteria are met, the system will choose the reflection correlating to the table and base its translation algorithm on this. A translation algorithms module is used to correlate the brightest hotspots coordinates with the position of the stage, and then commands the motors to rotate the stage so the new coordinates are (x:0, y:0). Knowing how far the hotspot is from the center, this function commands the motors to rotate the stage accordingly to move the hotspots to the center, to get the diamond properly aligned on the plate 750.

It will be appreciated that the x/y adjustment of the present invention as described herein allows the optimal hotspot pattern. As described herein, this process is automated and is run by software (application 17). The motor 1900 slowly drives the respective plate 1600, 1700 and captures images of the reflections (hotspots) and the processor of the present invention is configured to use image recognition software and the like to determine if the movement is resulting in a more optical hotspot pattern or the opposite in that the number of hotspots is decreasing as the plate moves linearly in this direction. The plates 1600, 1700 are moved incrementally until the optimal position is found in which the number of hotspots (reflections) is at a maximum.

As mentioned herein, the user can initiate the enter auto alignment process by simply pressing a button or otherwise inputting a command after the gemstone is initially centered using the manual alignment process (plunger or iris diaphragm). The user is then identified that the auto alignment process is completed once it is done.

The device 1000 includes a new glass stage to hold the stone, with the stage being controlled by 4 micro (servo) motors which in turn are controlled by the user through the application (software) running on a PC, or by an auto-alignment functionally in the application and software. There is an oscillating stage that allows for fine "z" adjustments to correct the angle of incidence between the laser and the diamond and the "x/y" stage allows the gemstone to be physically centered above the laser, in combination with software and the alignment can be down automatically as described herein.

As mentioned herein, the device 1000 utilizes image recognition to detect optimal alignment. Optical alignment occurs when: (1) the hotspot (laser reflection of the diamond table) is reflected back in the center of the projection screen, which is the laser source and (2) when the diamond is physically centered, resulting in the maximum amount of reflections. By utilizing image recognition, sophisticated algorithms, and motor controls, the system 1000 detects the total amount of light and the number of reflections of light, which allows for continuous and real-time monitoring of the amount of the hot spots, allowing the system to know when optimal alignment has occurred.

In yet another aspect, the device 1000 can be used as a gemstone simulant detector. More specifically, another use of the device 1000 is its ability to detect diamond simulants, by recognizing the differing refractive indices and optical properties of the most common diamond simulants, based on the reflection pattern of each gemstone. There are three main ways for the device 1000 to detect simulants. The first way is the shape of the reflections—in particular, diamonds generally produce a round reflection, whereas, the diamond simulants produce reflections that are knife-like, triangular, patchy, horse-tail shape, doubled and skeletal shaped. The second way is by analyzing the density of the reflections. Diamonds generally produce a dark consistent reflection, whereas, the diamond simulants produce grayish and duller reflections. The third way is by analyzing the size/standard deviation of the reflection size. Diamonds generally produce a uniform size of reflections, whereas diamond simulants tend to produce inconsistent and greatly varied reflection sizes for the same gemstone. These steps are performed by a processor executing code (software) (a gem stimulant analysis application contained in storage 19).

Based on the above parameters, the device 1000 is able to determine if the gemstone exhibits properties synonymous with a diamond, or one of its many simulants. More specifically, by using image recognition, the device 1000 is capable of analyzing the reflection pattern of the gemstone and by using software (application stored in storage 19), the processor by executing code can determine whether the gemstone is a diamond or whether it is acting more like a diamond simulant. In other words, if certain criteria are It will be understood that the present method is only for detection between a diamond and diamond simulants (i.e., cubic zirconia, moissanite, zircon, corundum, etc.). The device 1000 can have a separate operating mode for detection (i.e., a button on the display screen which can be selected) in which case, on a display screen, the processor can output an indicator as to whether the gemstone of the stage acts like a diamond or the not. This is important since this operating mode allows a sales clerk to make an immediate check of a gemstone that is being received and logged into the store's inventory. For example, the device 1000 has a small footprint and is easy and quick to operate and this allows the sales clerk to easily check the gemstone immediately when the customer drops the gemstone off to the sales clerk. If the gemstone exhibits properties that are more synonymous with diamond simulants, the customer is immediately notified and the sales clerk can refuse to take in the gemstone or can label the gemstone as such with the approval and under the direction of the customer.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A device for producing a reproducible identification pattern of a polished gemstone comprising:

a light source configured to direct a focused beam of light onto a gemstone orientated in a particular known manner to produce an output of the internal refraction and reflection characteristics of the gemstone including reflected light beams having particular locations, sizes and intensities;

a platform having a planar top surface to allow the gemstone to be oriented with its table facing down and seated against the planar top surface of the platform, the platform being formed of a material that allows the focused beam of light to pass therethrough and contact the gemstone disposed on the planar top surface;

a gimbal assembly for changing a position of the gemstone relative to the focused beam of light, wherein the gimbal assembly includes a first gimbal and a second gimbal, the first gimbal pivoting about a first axis and the second gimbal pivoting about a second axis that is perpendicular to the first axis, the platform being coupled to the second gimbal such that the platform extends across a center opening of the second gimbal, the first gimbal being rotatably coupled to a mount that is fixedly attached to a movable first plate that lies below the gimbal assembly, wherein the gimbal assembly is configured to tilt the platform on which the gemstone rests; and a device for recording the output in a manner to record at least one of the relative size and location of the reflected light beams.

2. The device of claim 1, wherein the first gimbal comprises an outer gimbal and the second gimbal comprises an inner gimbal that is disposed within the outer gimbal.

3. The device of claim 2, wherein the first gimbal includes a notch through which a portion of the second gimbal passes to permit attachment of the second gimbal to a part that is external to the first gimbal.

4. The device of claim 3, wherein the portion of the second gimbal comprises a coupling member that couples the first gimbal to the part that is external to the first gimbal.

5. The device of claim 4, wherein the part that is external to the first gimbal comprises a device that controllably pivots the second gimbal within the first gimbal.

6. The device of claim 5, wherein the device that controllably pivots the second gimbal comprises a motor.

7. The device of claim 1, wherein the movable first plate is part of a centering mechanism for centering the gemstone along both an x axis and a y axis, the movable first plate including an opening through which the focused beam of light passes.

8. The device of claim 5, wherein the movable first plate is part of a centering mechanism for centering the gemstone along both an x axis and a y axis, the first plate including an opening through which the focused beam of light passes, the gimbal assembly being mounted to the movable first plate such that movement of the movable first plate is translated into movement of the gimbal assembly.

9. The device of claim 8, further including a movable second plate to which the movable first plate is slidably mounted, the movable second plate being coupled to a gimbal base such that the second plate can move relative thereto.

10. The device of claim 9, wherein the gimbal base includes a first opening through which the focused beam of light passes and a second opening which permits viewing of a screen that is below the gimbal base and on which the output is cast.

11. The device of claim 9, wherein the movable first plate moves along a first linear direction and the movable second plate moves along a second linear direction.

12. A device for producing a reproducible identification pattern of a polished gemstone comprising:

a light source configured to direct a focused beam of light onto a gemstone orientated in a particular known manner to produce an output of the internal refraction and reflection characteristics of the gemstone including reflected light beams having particular locations, sizes and intensities;

a platform having a planar top surface to allow the gemstone to be oriented with its table facing down and seated against the planar top surface of the platform, the platform being formed of a material that allows the focused beam of light to pass therethrough and contact the gemstone disposed on the planar top surface;

a gimbal assembly for changing a position of the gemstone relative to the focused beam of light, wherein the gimbal assembly includes a first gimbal and a second gimbal, the first gimbal pivoting about a first axis and the second gimbal pivoting about a second axis that is perpendicular to the first axis, the platform being coupled to the second gimbal such that the platform extends across a center opening of the second gimbal, the gimbal assembly being mounted to a first sliding plate that is part of an automated centering mechanism and moves in a horizontal direction along a first axis; and a device for recording the output in a manner to record at least one of the relative size and location of the reflected light beams.

13. The device of claim 12, wherein each of the first and second gimbals is driven in a controlled and automated manner.

14. The device of claim 13, wherein the first gimbal is operatively connected to a first motor and the second gimbal is operatively connected to a second motor.

15. The device of claim 12, wherein the first gimbal comprises an outer gimbal and the second gimbal comprises an inner gimbal that is disposed within the outer gimbal.

16. The device of claim 12, wherein the first gimbal includes a notch through which a portion of the second gimbal passes to permit attachment of the second gimbal to a part that is external to the first gimbal.

17. The device of claim 16, wherein the part that is external to the first gimbal comprises a motor which controllably drives the second gimbal.

18. The device of claim 12, wherein the first axis is an x axis and the first sliding plate moves a prescribed distance along the x axis so as to change a position of the gemstone along the x axis and a second sliding plate that moves a prescribed distance along the y axis so as to change a position of the gemstone along the y axis, the first slide plate and the second slide plate comprising the automated centering mechanism.

19. The device of claim 18, wherein the first sliding plate is disposed over the second sliding plate but is movable (in the x direction) relative thereto, the first sliding plate being directly coupled to the underlying second sliding plate.

20. The device of claim 18, wherein the first sliding plate is operatively coupled to a first drive member for moving the first sliding plate a first prescribed distance in both a positive direction and a negative direction along the x axis, the second sliding plate being operatively coupled to a second drive member for moving the second sliding plate a second prescribed distance in both a positive direction and a negative direction along the y axis.

21. The device of claim 12, wherein the automated centering mechanism further includes a second sliding plate that moves in the horizontal direction along a second axis.

22. The device of claim 21, wherein the first and second axes are perpendicular to one another.

23. The device of claim 21, wherein the device for recording the output comprises a camera that is located above the gimbal assembly and is positioned to record a screen that is located below the gimbal assembly and on which the output is recorded.

* * * * *